(12) United States Patent
Neilan et al.

(10) Patent No.: US 11,846,016 B2
(45) Date of Patent: Dec. 19, 2023

(54) MEDICAL DEVICE WITH PLASMA MODIFIED OXIDE LAYER AND METHOD OF FORMING SUCH A DEVICE

(71) Applicant: Cook Medical Technologies LLC, Bloomington, IN (US)

(72) Inventors: John Neilan, Gort (IE); David Murray, Limerick (IE); James Butler, Aherlow (IE)

(73) Assignee: Cook Medical Technologies LLC, Bloomington, IN (US)

(*) Notice: Subject to any disclaimer, the term of this patent is extended or adjusted under 35 U.S.C. 154(b) by 0 days.

(21) Appl. No.: 17/543,054

(22) Filed: Dec. 6, 2021

(65) Prior Publication Data
US 2022/0235454 A1 Jul. 28, 2022

Related U.S. Application Data

(62) Division of application No. 16/200,870, filed on Nov. 27, 2018, now Pat. No. 11,193,202.
(Continued)

(30) Foreign Application Priority Data
Nov. 27, 2017 (GB) ..................... 1719689

(51) Int. Cl.
*A61F 2/82* (2013.01)
*A61L 31/02* (2006.01)
(Continued)

(52) U.S. Cl.
CPC ........... *C23C 16/0227* (2013.01); *A61F 2/82* (2013.01); *A61L 27/06* (2013.01); *A61L 27/306* (2013.01);
(Continued)

(58) Field of Classification Search
CPC ............................. A61F 2/82; A61F 2210/001
See application file for complete search history.

(56) References Cited

U.S. PATENT DOCUMENTS

| 2006/0134211 A1* | 6/2006 | Lien | ..................... A61K 31/337 424/472 |
| 2010/0055145 A1* | 3/2010 | Betts | ..................... A61L 31/10 424/423 |

(Continued)

FOREIGN PATENT DOCUMENTS

EP         0606566 A1 *  7/1994

OTHER PUBLICATIONS

Aronsson et al. "Glow Discharge Plasma Treatmetn for Surface and Cleaning Modification of Metallic Biomaterials," Journal of Biomedical Materials Research, vol. 35Apr. 1, 1997, pp. 46-73. (Year: 1997).*

*Primary Examiner* — Cachet I Proctor
(74) *Attorney, Agent, or Firm* — Woodard, Emhardt, Henry, Reeves & Wagner, LLP

(57) ABSTRACT

A method of modifying a surface of a medical device for implantation or disposition inside a patient is described. The medical device comprises a structure having at least one surface. The method includes the steps of: placing the medical device into a plasma chamber substantially free from contaminants and substantially sealing the plasma chamber from the atmosphere; removing at least an outermost layer of any oxide layer from the at least one surface of the structure by a plasma oxide-removal process, whilst maintaining the plasma chamber under seal from the atmosphere; and subsequently forming a new oxide layer at the least one surface of the structure by introducing at least one gas into the plasma chamber, whilst maintaining the plasma chamber under seal from the atmosphere. A medical device including a bulk material and an oxide layer disposed over
(Continued)

at least one surface of the medical device. The oxide layer is substantially pure and free from contaminants.

19 Claims, 15 Drawing Sheets

Related U.S. Application Data

(60) Provisional application No. 62/590,884, filed on Nov. 27, 2017.

(51) Int. Cl.
| | |
|---|---|
| *C23C 16/02* | (2006.01) |
| *A61L 31/08* | (2006.01) |
| *A61L 31/16* | (2006.01) |
| *A61L 27/30* | (2006.01) |
| *A61L 27/06* | (2006.01) |
| *A61L 27/54* | (2006.01) |
| *C23C 16/40* | (2006.01) |
| *C23C 16/50* | (2006.01) |
| *H01J 37/32* | (2006.01) |

(52) U.S. Cl.
CPC ............ *A61L 27/54* (2013.01); *A61L 31/022* (2013.01); *A61L 31/088* (2013.01); *A61L 31/16* (2013.01); *C23C 16/40* (2013.01); *C23C 16/50* (2013.01); *H01J 37/32449* (2013.01); *H01J 37/32513* (2013.01); *A61F 2210/0014* (2013.01); *A61F 2210/0076* (2013.01); *A61F 2240/001* (2013.01); *A61F 2250/0067* (2013.01); *A61L 2300/416* (2013.01); *A61L 2400/18* (2013.01); *A61L 2420/02* (2013.01); *H01J 2237/335* (2013.01); *H01J 2237/3321* (2013.01)

(56) References Cited

U.S. PATENT DOCUMENTS

2011/0172763 A1* 7/2011 Ndondo-Lay ......... A61L 31/022
623/1.42
2017/0203011 A1* 7/2017 Neilan .................... A61L 29/04

* cited by examiner

C1s graph (C-C at 284.8 eV, C-O & C-OH at 286.0 eV, C=O at 287.5 eV, O-C=O at 288.5 eV)

C1s bar

Ti 2p graph (Ti Metal at 454.1 eV, TiO 455.2 at eV, Ti2O3 at 457.2 eV, TiO2 at 458.6 & 464.4 eV)

Ti 2p bar

O1s graph (TiO2 at 529.9 eV, Ti-OH at 531.3 eV, C-O at 532.2 eV, C=O at 533.0 eV)

O1s bar

| Stent | Machine | Power (W) | Gases: | Pressure: (mbar) | Process time (min) | Waiting time before venting (min) | Venting gas |
|---|---|---|---|---|---|---|---|
| A | Model Diener Pico 13.56MHz generator Quarz glass chamber | 300 | Ar/H2 (50%/50%) | 0.4 | 30 | 30 | O2 |
| B | | | Ar/H2 (50%/50%) | | 60 | 60 | |
| C | | | Ar/H2 (33%/66%) | | 60 | 15 | |
| D | | | Ar | | 60 | 15 | |

XPS data for surface of Stent A as received (original) vs treated

XPS data for surface of Stent B as received (original) vs treated

XPS data for surface of Stent C as received (original) vs treated

XPS data for surface of Stent D as received (original) vs treated

XPS data for plasma cleaned surface as received (original) vs treated

MEDICAL DEVICE WITH PLASMA MODIFIED OXIDE LAYER AND METHOD OF FORMING SUCH A DEVICE

CROSS REFERENCE TO RELATED APPLICATIONS

This application claims the benefit of Great Britain patent application No. 1719689.0 filed on Nov. 27, 2017 and U.S. provisional patent application No. 62/590,884 filed on Nov. 27, 2017 both entitled "Medical Device with Plasma Modified Oxide Layer and Method of Forming Such a Device" the entire contents of which are incorporated herein by reference.

TECHNICAL FIELD

The present invention relates to a medical device having a plasma modified oxide layer and to a method of preparing such a device. The invention can be used with endoluminally deployable implantable medical devices such as stents, stent grafts, vascular filters and plugs, prostheses and the like. In particular the invention relates to a stent. In particular the invention relates to implantable medical devices formed from metal. By modifying the oxide layer at the surface of the device, its corrosion resistance may be optimised or improved. One aspect of the invention relates to a coated medical device and to improving or optimising an oxide layer of the medical device in order to improve the retention of bioactive materials on the medical device without the need for a containment or time release mechanism.

BACKGROUND ART

The properties and behaviour of a medical device are in part determined by the material of their bulk, and in part determined by the nature of a layer at their surface and the exposed surface of that layer. The word surface is used herein to refer to both the exposed surface and the layer at the surface.

After manufacturing a device the surface of the device may be contaminated by environmental contaminants or by contaminants from the manufacturing and even cleaning processes. Such contaminants can, over time, lead to corrosion of the device. Deposits of contaminants, such as, for example calcium, at the surface and in the layer below the surface may act as channels for corrosion to propagate into the body of a medical device. This can in turn lead to stent fracture, nickel ion release, adverse tissue responses and ultimately failure of the device.

Contaminants at the surface may also lead to difficulties in coating the device, for example with a bioactive agent. Implantable medical devices, particularly endoluminally deployable medical devices, are known for a variety of medical applications. In the case of an implantable medical device, that is a device intended to be left in the patient permanently or over long periods of time, the device may be coated with one or more layers of drug intended for long term drug administration to diseased tissue. Treatment of cancers is an example. In other examples, the coating is provided in order to treat adverse body reactions caused by the medical treatment or by long term presence of a foreign object in the body, such as initial reactive hyperplasia, restenosis and so on. In these cases the medical device may be deployed only temporarily or long term in a patient.

It is important that a bioactive coating on a medical device is consistent over the surface or surfaces of the device, is reliably formed from one device to another, is sufficiently well held on the device during deployment, and can be administered into the patient at the desired rate once the device is deployed. For instance, a coating on an implantable device such as a stent, filter, vascular plug or the like may need to be released over an extended period of time such as weeks, months or years, whereas a coating on a medical balloon, such as an angioplasty balloon or a device delivery balloon, may need to be released over a period of seconds or minutes.

Applying a bioactive agent to an untreated surface of a medical device often fails to form a uniform or reliable coating, leading to variable therapeutic results. This is particularly the case with lipophilic materials including, for instance, paclitaxel, which has been proven to be a very effective anti-proliferative agent (anti-restenosis drug) as well as a cancer treatment drug.

Attempts have been made in the art to treat one or more surfaces of medical devices to improve their biocompatibility and also to seek to improve the adherence of one or more bioactive coatings onto the medical device. These known treatments, however, have failed to provide consistent, reliable and repeatable surface characteristics for many bioactive agents. Inadequate or non-reliable coatings can result in failure to meet the strict drug release requirements of the FDA USP pharmacopeia standards and those of other regulatory bodies.

Other attempts in the art have involved providing for containment of the bioactive agent, for instance in a containment device such as a polymer matrix, by applying an outer layer or coat over the layer of bioactive material, by encapsulating the bioactive agent in capsules or other carriers, and so on. Such containment mechanisms, which restrain the bioactive material on the device and control the release of the material into the patient, can often cause other clinical issues, including reduction in the amount of bioactive material which can be carried on the medical device and inadequate release rate of the bioactive material. Furthermore, the containment device can act as a target for long term restenosis and other foreign body reactions. Despite such drawbacks, containment devices are still often proposed in order to seek to overcome the difficulty of adequately holding the bioactive material to the medical device and of ensuring adequate dosage of bioactive material in order to try to meet regulatory criteria.

Some examples of known surface treatments are disclosed in U.S. Pat. Nos. 7,597,924, 7,396,582, 6,632,470, 8,123,799, 9,005,960 and US-2009/171453.

SUMMARY OF THE INVENTION

The present invention seeks to provide an improved medical device and method of preparing such a device. One aspect of the invention seeks to provide a more corrosion resistant medical device and method of preparing such a device. Another aspect of the invention seeks to provide an improved coated medical device and method of preparing and coating such device.

According to an aspect of the present invention, there is provided a method of modifying a surface of a medical device for implantation or disposition inside a patient, the medical device comprising a structure having at least one surface, the method including the steps of:

placing the medical device into a plasma chamber substantially free from contaminants and substantially sealing the plasma chamber from the atmosphere;

removing at least an outermost layer of any oxide layer from the at least one surface of the structure by a plasma oxide-removal process, whilst maintaining the plasma chamber under seal from the atmosphere; and subsequently forming a new oxide layer at the at least one surface of the structure by introducing at least one gas into the plasma chamber, whilst maintaining the plasma chamber under seal from the atmosphere.

The inventors have discovered that a significant increase in corrosion resistance and improved adhesion characteristics can be achieved by removing at least part of a naturally occurring oxide layer from the surface of a medical device and forming a new purer oxide layer at that surface. Contamination may reside on the outermost surface of the device, and may also penetrate into an outer layer of any oxide layer. Removal of the outermost layer of any oxide layer may therefore result in removal of contamination from the surface of the device. By carrying out both the removal and regrowth steps in the controlled environment of a plasma chamber the new oxide layer formed at the surface of the medical device is extremely pure, having significantly less contamination than a naturally occurring oxide layer.

Preferably the new oxide layer is a stronger and more uniform lewis acid or base (or amphoteric species) compared to the oxide layer removed in the plasma oxide-removal process. In the preferred embodiments, the new oxide layer has an increased acidic polar or base polar (or amphoteric species) composition compared to a remainder of the structure of the medical device. The oxide layer modification taught herein may amplify the desired polar surface energy while suppressing other non-polar components of the surface energy. As a result, the surface may be more easily and reliably coated with a bioactive material. It is not necessary to restrain the (bioactive) material in any containment mechanism, such as a containment polymer, matrix or the like.

The steps of removing any oxide layer from the at least one surface, and forming a new oxide layer at the least one surface, may be carried out whilst substantially preventing contaminants from entering the plasma chamber. A sacrificial oxygen getter may be placed inside the plasma chamber so as to reduce the amount of oxygen reaching the surface of the structure in the case of air leakage into the plasma chamber.

Advantageously, the plasma chamber includes a vacuum pump for drawing matter from the plasma chamber. Advantageously the plasma chamber also includes a hydrogen source and valve for controlling the flow of hydrogen into the chamber. Preferably the plasma chamber includes an argon source and valve for controlling the flow of argon into the chamber. The plasma chamber may include further gas sources and valves for introducing gas or a mixture of gases into the plasma chamber.

The plasma oxide-removal process may include the steps of:

drawing down a vacuum in the plasma chamber;

introducing at least one of hydrogen and argon gas into the plasma chamber; and supplying energy to the plasma chamber so as to create plasma in the chamber to remove at least an outer layer of any oxide layer from the at least one surface of the structure.

Drawing down a vacuum may be accomplished by activating a vacuum pump to draw matter out of the plasma chamber. The plasma chamber may be filled with an oxygen-free blanket gas, such as hydrogen, argon or another inert gas, during the plasma oxide-removal process.

Where hydrogen gas is introduced into the plasma chamber and energy is supplied to the chamber, hydrogen plasma is created. Hydrogen plasma includes stimulated hydrogen molecules, ions and radicals. These react with the oxygen in any oxide layer, forming water vapour which can be removed from the plasma chamber by a vacuum pump.

Where argon gas is introduced into the plasma chamber and energy is supplied to the chamber, argon plasma is created. Argon plasma includes argon ions. The ions are accelerated by the electric field of the plasma chamber, bombarding the surface and in effect sandblasting contaminants off the surface. The contaminants may then be removed from the plasma chamber by a vacuum pump.

The plasma oxide-removal process may be carried out at a temperature below about 300° C., preferably at a temperature below 100° C. The step of forming a new oxide layer may be carried out at a temperature below about 300° C., preferably at a temperature below 100° C. The plasma oxide-removal process may be carried out for up to about 60 minutes. The plasma oxide-removal process may be carried out for between about 30 and 60 minutes. The plasma oxide-removal process may be carried out for between about 15 and 45 minutes. The plasma oxide-removal process may be carried out for between about 5 and 15 minutes. The plasma oxide-removal process may be carried out for around 30 minutes, such as for example between 25 and 35 minutes.

After plasma removal of the oxide layer, the energy supply may be deactivated or switched off so no further plasma is created in the chamber. The energy supply may remain deactivated or switched off whilst the new oxide layer is grown on the surface. In other words the plasma may be switched off whilst the new oxide layer is grown. This allows natural, spontaneous growth of the oxide layer in a pure environment. This naturally grown layer can be thinner, more stable, and therefore less likely to corrode than one grown in a plasma environment. The vacuum pump may remain activated so as to remove matter from the plasma chamber after removal of the oxide layer.

The plasma chamber may include an oxygen valve for introducing oxygen gas into the plasma chamber. The step of forming a new oxide layer may be carried out by introducing a gas or gas mixture into the plasma chamber, the gas or gas mixture selected so as to produce a new oxide layer having a desired surface energy profile. The step of forming a new oxide layer may be carried out by introducing pure oxygen gas into the plasma chamber. The step of forming a new oxide layer may be carried out by introducing pure oxygen and argon gases into the plasma chamber. The step of forming a new oxide layer may be carried out whilst the vacuum pump is activated. After the oxide layer has been formed the vacuum pump may be switched off and the plasma chamber may be vented, preferably with pure oxygen as the air around the chamber is often contaminated.

As the process is carried out in the plasma chamber which is relatively free from contamination, the new oxide layer is extremely pure and substantially free from contaminants.

Preferably, the new oxide layer is substantially free from at least one of carbon, calcium and silicon. The silicon may be in the form of an oil. Preferably, at least one of carbon, calcium and silicon, if present, are only present at levels undetectable by X-ray Photoelectron Spectroscopy (XPS). This can ensure that the characteristics of the oxide layer and of the structure in general are optimised and not compromised by carbon and/or calcium as an impurity in the chemical structure of the device. It is to be understood that the term "carbon/calcium free" is intended to mean absolutely or substantially free of carbon and/or calcium, that is that in some manufacturing instances it may be impossible to eliminate carbon/calcium (or other impurities) totally but that any carbon/calcium (or other impurity) on the device is of a sufficiently small amount as not to have any noticeable practical effect on the performance of the structure and in particular on the uniformity of the oxide or the characteristics of any bioactive coating thereon. In some cases silicon contamination may result when using a glass plasma chamber. This silicon contamination is acceptable as it is silicon dioxide and does not significantly affect the corrosion resistance or drug coating adhesion of the surface. The silicon on the original stent is usually an oil, causes problems, and is unwanted contamination.

Preferably the step of forming a new oxide layer is carried out until the oxide layer is between around 3 and 18 nanometres in thickness. In more preferred embodiments the oxide layer is between around 6 and 18 nanometres in thickness, even more preferably between around 8 and 12 nanometres in thickness. The newly formed oxide layer may be between 2 nm and 50 nm thick. The inventors have found that there is an optimum thickness to the oxide layer in accordance with the teachings herein. This is a balance between uniformity of the oxide layer, in particular of its polar acid or base characteristics, and having an oxide layer which is too thick. Preferably the oxide layer is of sufficient thickness to ensure nickel and nickel oxide are not present on the surface. An excessively thick oxide layer can be brittle and as a result adversely affect the performance and reliability of the stent in use.

In some embodiments, the oxide growing step is carried out in an atmosphere with the addition of an acidic or basic component, for instance including one or more of: magnesium, aluminium, cerium, zinc, molybdenum, tungsten, niobium, tantalum, vanadium, zirconium. In this manner, a polar acid or polar base component can be introduced as a dopant to the oxide of the structure during the formation of the oxide layer.

Optionally the method may include a passivation step after the oxide regrowth step. The passivation step may include thermally passivating the part in air or oxygen at a temperature up to around 300 C for up to around 1 hour. This may take place in the plasma chamber or in a separate oven. The passivation step may include chemically passivating the part with water or a 30% aqueous solution of hydrogen peroxide and boiling for up to about 1 hour. The passivation step may include chemically passivating the part with 10% nitric acid solution at room temperature, according to the ASTM-F86 standard.

The medical device may be formed from at least one of nickel titanium alloy, stainless steel and cobalt chromium steel. A nickel titanium alloy may be nitinol. Where the structure is formed of a nickel titanium alloy, the method may optimise the growth of a titanium oxide layer on the at least one surface in preference to nickel or nickel oxide. Where the structure is formed of stainless steel, the method may optimise the growth of a $Cr_2O_3$ dominant oxide layer on the at least one surface. Where the structure is formed of cobalt chromium steel, the method may optimise the growth of a $Cr_2O_3$ oxide layer on the at least one surface.

The plasma oxide-removal process may remove the entire oxide layer from the at least one surface. As such the bulk material may be exposed. Removal of the entire oxide layer may provide the optimum exposed surface on which to regrow the new oxide layer.

The structure of the medical device may comprise a sublayer under any oxide layer at the at least one surface. In this case the method may include the step of removing the sublayer by a plasma sublayer-removal process, whilst maintaining the plasma chamber under seal from the atmosphere. This step is carried out before forming a new oxide layer on the at least one surface. Where the structure is formed from a nickel titanium alloy, the sublayer may be a nickel rich sublayer.

The medical device may be or include a stent or other support scaffold structure. The medical device may be of any of the varieties described above and elsewhere in this specification. Where the medical device is a stent or has a similar support member or scaffold the medical device may be made of a metal or metal alloy, such as a nickel titanium alloy. The stent could equally be made of other materials known in the art.

The method may include the pre-step of subjecting the structure to an electropolishing process thereby to remove at least some of any oxide layer on the at least one surface of the structure and any contamination, debris or sharp edges on the surface of the structure from manufacturing the device.

The electropolishing process may provide a bath of electropolishing fluid and an inert gaseous blanket over the electropolishing fluid bath. The inert gaseous blanket may be an argon or nitrogen blanket. The blanket is provided in order to avoid the formation of uncontrolled oxides on the structure, which can lead to non-uniform and therefore unreliable surface characteristics to the structure, leading in turn to unreliable material coatings. The electropolishing process may be carried out in an oxygen free environment. The electropolishing process may remove at least 2%, of the structure by weight. The electropolishing process may remove at least 10% of the structure by weight.

Preferably the method includes a neutralisation step, following electropolishing, so as to remove electropolishing residue from the structure. The neutralising step is advantageously carried out in an oxygen free base bath.

The method may also include the step of cleaning the at least one surface with an alcohol prior to electropolishing, in order to remove grit, grease and other contaminants from the manufacturing processes at the surface. Advantageously, the step of cleaning the at least one surface with alcohol is carried out prior to any atomic cleaning of the surface. Ethanol is a suitable cleaning agent for this step.

The method preferably includes the step of applying a coating of the at least one surface, wherein the coating:
  a) consists of or is principally of bioactive material;
  b) is or includes a therapeutic substance;
  c) is or includes an anti-proliferative bioactive substance; or
  d) is or includes paclitaxel.

The oxide layer is preferably substantially impervious to the material coating. In other words, it is preferred that the bioactive material is in the form of a distinct layer overlying the oxide layer and preferably does not penetrate at all, or only minimally, into the oxide. The coating may include an excipient, such as urea.

In preferred embodiments, the coating is free of one or more of:
  a) containment elements;
  b) binding agents; and
  c) time control release agents;
  d) polymer or other matrix material.

According to an aspect of the present invention a medical device is provided having a structure for implantation or disposition inside a patient, the structure including:
  a bulk material; and an oxide layer disposed over at least one surface of the medical device;

wherein the oxide layer is substantially pure and free from contaminants.

The oxide layer may include the addition of an acidic or basic component as a doping agent, such as one or more of: magnesium, aluminium, cerium, zinc, molybdenum, tungsten, niobium, tantalum, vanadium, zirconium.

In some embodiments, the bulk material of the structure is modified, for instance by forming the structure to include at least one acidic or basic polar constituent in the bulk material. This may be as a dopant or as an alloying element. The acidic or basic component may include one or more of: magnesium, aluminium, cerium, zinc, molybdenum, tungsten, niobium, tantalum, vanadium, zirconium. This component will be drawn to the surface of the bulk material and become a part of the oxide of the structure during oxidation and therefore act to give the oxide layer a polar acid or polar base character.

An aspect of the present invention provides a Nitinol stent treated by the disclosed method having an oxide layer having an acidic polar surface energy in the region of at least 3.7 Dynes/cm and no measurable basic polar surface energy.

The method of the present invention may include the step of hydroxylating the surface of the oxide layer.

Other aspects and advantages of the teachings herein are described below in connection with the preferred embodiments disclosed herein.

BRIEF DESCRIPTION OF THE DRAWINGS

Embodiments of the present invention are described below, by way of example only, with reference to the accompanying drawings, in which:

FIG. 16 is a table showing treatment conditions for four stents, A, B, C and D in a plasma chamber whilst removing the oxide layer from the surface of the stents and regrowing a new oxide layer at that;

FIGS. 17-20 show XPS data for the surfaces of stents A, B, C and D cited in the table of FIG. 16.

DESCRIPTION OF THE PREFERRED EMBODIMENTS

Figure 1:
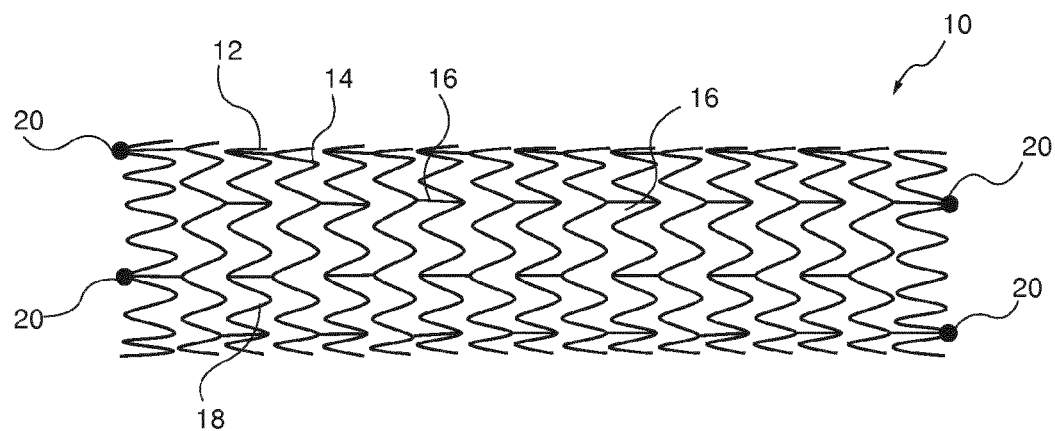
FIG. 1 is a side elevational view of an exemplary vascular stent.

It is to be understood that the drawings are schematic only and not to scale. Often only the principal components relevant to the teachings herein are shown in the drawings, for the sake of clarity.

The embodiments described below focus on a stent, in particular, a coated stent. It is to be understood, however, that these are examples only and that the teachings herein can be applied to a large range of medical devices, both for temporary placement in a patient and also for long term placement. Other examples include stent grafts, vascular filters and plugs, valvuloplasty devices, prostheses and so on.

Referring first to FIG. 1, there is shown an exemplary vascular stent 10 to which the teachings herein can be applied. The stent 10 is generally a tubular structure 12, in this example formed of a plurality of stent rings 14 which extend in series coaxially along the length of the tubular structure 12 and are coupled to one another by means of tie bars 16, as is well known in the art. In this example, the stent rings 14 are formed of a plurality of strut sections 18 arranged a zigzag shape. At the end of the stent 10 there may be provided radiopaque markers 20, again of a type well known in the art.

The stent 10 may be self-expanding or balloon expandable and made of any suitable material, of which many are known in the art. Examples of suitable materials are given below.

Figure 2:
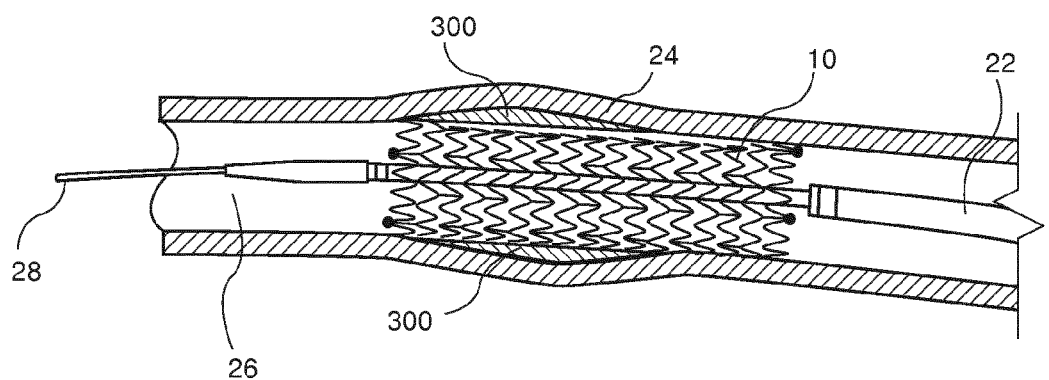
FIG. 2 is a schematic representation of the stent of FIG. 1 in the process of being deployed in a patient's vessel to treat a stenosis.

Referring also to FIG. 2, the stent 10 can be seen in the process of being deployed into a vessel 24, by means of an introducer assembly of which the distal end components 22 are visible in FIG. 2. These typically include a carrier element having a dilator tip 26 at the distal end thereof. The dilator tip 26 has a lumen therein for the passage of a guide wire 28. The components of the introducer assembly are not relevant to the teachings herein.

In the example in FIG. 2, the stent 10 is being deployed in order to treat a stenosis 300 of the vessel 24 and also to keep the vessel 24 open for the passage of blood therethrough.

FIG. 6 shows XPS depth profiling of a number of off-the-shelf nitinol stents at 0 Å and 6 Å. An oxide layer on a bulk metal has a depth, and a surface onto which a coating may be applied. The oxide layer includes an outermost layer adjacent the surface of the layer. The outermost layer may have a different composition and therefore different properties from the rest of the oxide layer. The oxide layer of a nitinol stent includes titanium dioxide, the thermodynamically unstable titanium monoxide and nickel oxides. The outermost layer of the oxide is generally mainly titanium dioxide. At the exposed surface titanium hydroxide, contamination and water can be seen via various techniques. If the pressure/humidity/temperature favour it, a water layer may form over the hydroxide layer. FIG. 7A is a schematic view of the oxide layer on pure titanium. The distinction between the bulk metal and the oxide layer can be clearly seen, as well as the difference between the oxide layer and the surface of the oxide. FIG. 7B is a schematic view of a structurally ordered $TiO_2$ surface with two types of hydroxides, acidic and basic hydroxides, extending out from the surface. The presence of hydroxyl groups at the surface may enable better bonding of a bioactive material coating to the surface. The hydroxyl groups may bond to the bioactive material by hydrogen bonding. As such the hydroxyl groups may act as lewis acids or lewis bases.

Figure 6A:
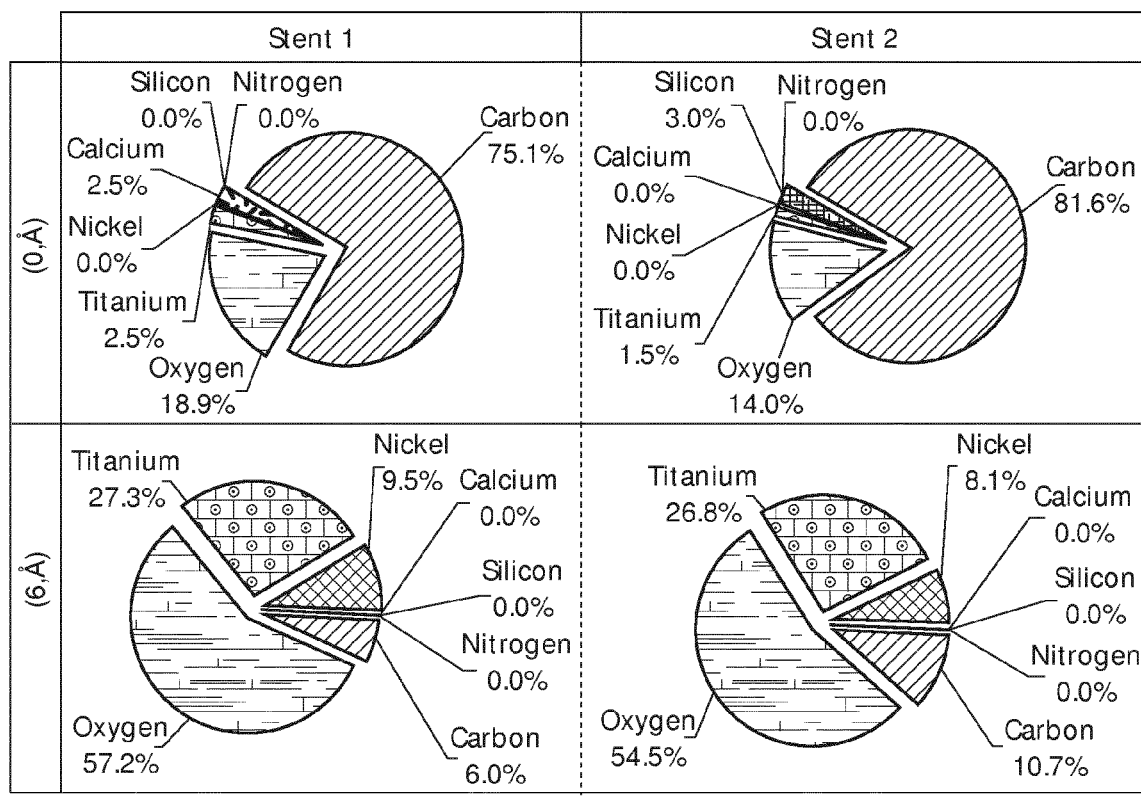
FIGS. 6A and 6B show XPS depth profiling of a number of nitinol stents.
Figure 6B:
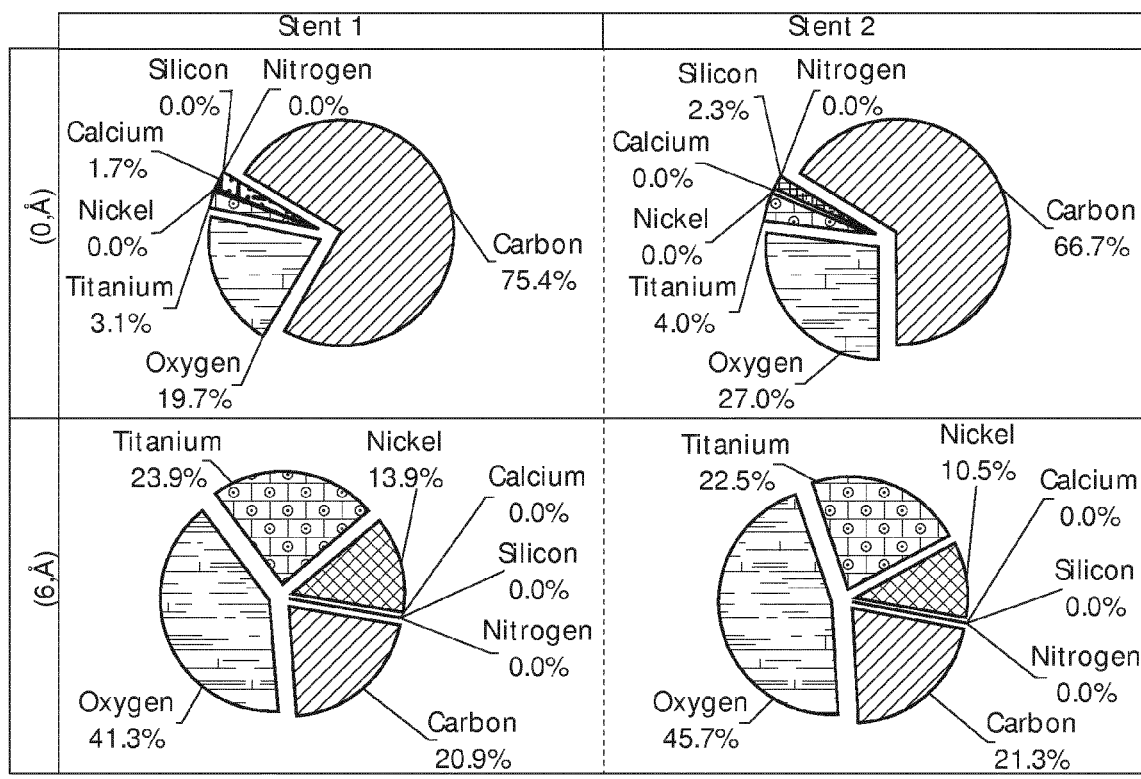
Figure 7A:
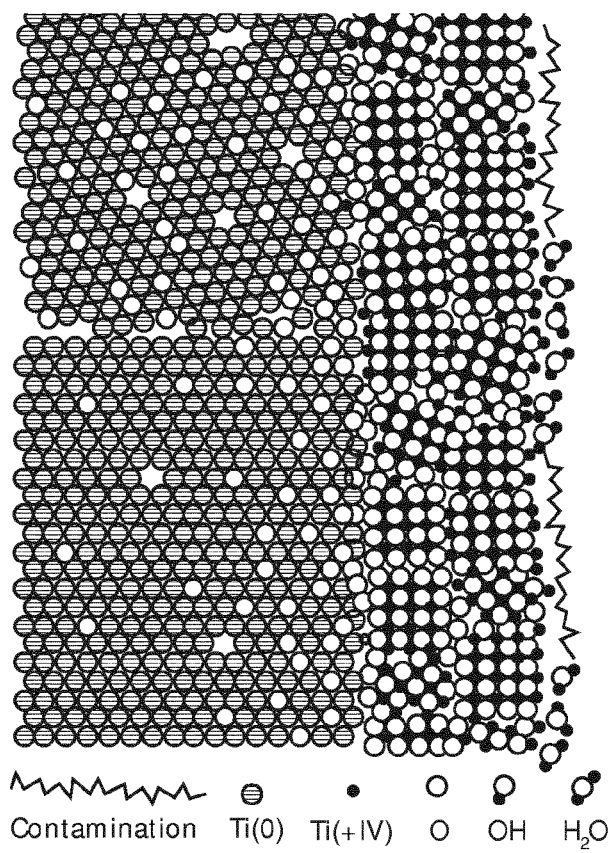
FIG. 7A is a schematic view of the oxide layer on pure titanium
Figure 7B:
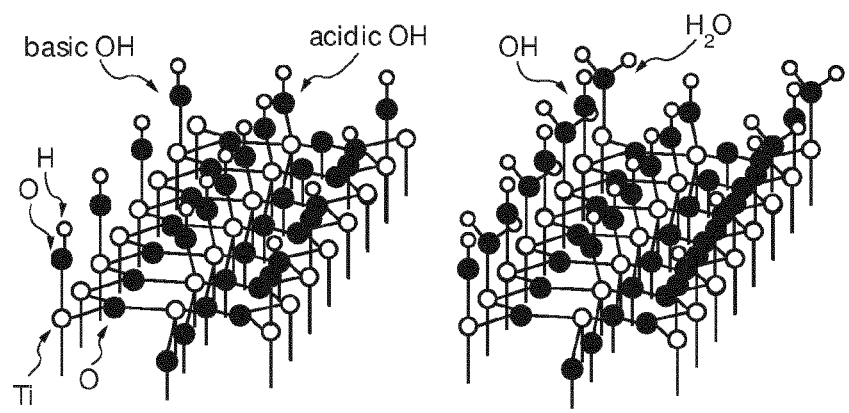
FIG. 7B is a schematic view of a structurally ordered $TiO_2$ surface with two types of hydroxides, acidic and basic hydroxides.

In FIG. 6, the XPS results at 0 Å show the composition of the outermost surface layer and the results at 6 Å show the composition of the bulk oxide on nitinol stents. The results show, that the bulk oxide includes between 6.0-10.7% carbon contamination in the stents profiled in FIG. 6A, and between 20.9-21.3% carbon contamination in the stents profiled in FIG. 6B.

The oxide forms spontaneously after electropolishing. Unfortunately, the oxide is always contaminated by either environmental contaminants or by contaminants from the electropolishing bath. Carbon contamination from the atmosphere or residuals from the electropolishing bath can account for a significant proportion of the oxide. Calcium deposits may also be present in the oxide which are also from residuals in the electropolishing bath. Carbon and silicon oil contamination reduces the adherence of paclitaxel and other drugs to the surface of the stent, whilst calcium deposits act as channels for corrosion to propagate into the stent. For a nitinol stent the surface of the oxide layer, the surface onto which a drug will be coated, may include titanium hydroxide and titanic acids which are formed when the surface is exposed to air and/or moisture. Hydroxide groups and water may also be present at the surface. Contaminants may be adsorbed at the surface.

The inventors have discovered that careful control of the formation of an oxide on the surfaces of the bulk structure of the medical device can result in substantially pure oxide layer at the surface which has a number of advantages. Firstly, by having a purer oxide layer the device may have improved corrosion resistance. Secondly, by having an even, substantially contaminant free surface the surface of the device may bind more effectively to a coating placed on the surface, such as a pharmaceutical drug coating.

Often, the deployment of a stent alone in the vessel does not provide a permanent solution as closure of the vessel can reoccur, such as by restenosis. This can be caused by a number of factors, including damage to the tissue of the vessel 24 during the vessel opening or angioplasty procedure, reoccurrence of the original causes of the stenosis, body reaction to the presence of a foreign body in the vessel, and so on.

In the example described briefly above in connection with FIG. 2, it has been found that the administration of suitable bioactive agents into the vessel wall from the stent can substantially retard or prevent subsequent closure of the vessel due to restenosis. Bioactive agents released from the stent can also treat many other medical conditions, including the original disease of the tissue. A variety of bioactive agents suitable for such purposes are known in the art including, for instance, anti-thrombogenic agents, thrombin inhibitors, tissue plasminogen activators, thrombolytic agents, fibrinolytic agents, vasospasm inhibitors, antiplatelet agents, anti-proliferative agents and so on. A particularly effective bioactive agent known in the art is paclitaxel, others including dexamethasone, heparin and numerous other agents and compounds. A list of suitable bioactive agents is given at the end of this specification, though it is to be understood that the list is not exhaustive.

The bioactive material is coated onto the medical device, for example the stent 10 of FIG. 1, so as to be released from the medical device into the tissues of the vessel 24, and should be dispensed at a rate suitable for treating the required medical condition. In the case of a stent or other implantable medical device, it may be desirable for the bioactive material to be released over a prolonged period of time, for example weeks or months. In the case of a medical device that is temporarily deployed in a patient's vessel, the bioactive agent should typically be released from the device in a very short period of time, for instance within seconds or minutes, although sometimes could be up to an hour or more.

It is important that the bioactive agent is held onto the medical device during deployment of the device in the patient without excessive loss of bioactive material into the patient's bloodstream, for instance. For this purpose, the prior art has suggested restraining the bioactive material, for instance in a containment or time release layer or matrix. Examples include: porous polymer layers into which bioactive material can be embedded, enclosed chambers holding the bioactive material, outer coatings disposed over the bioactive material and which dissolve or open during the deployment process, encapsulation of the bioactive material in capsules or pellets, and so on. Such containment measures can lead to a number of disadvantages, including undesirable delayed administration of the bioactive material into body tissues, presence of a foreign substance in the body, possible onset of stenosis caused by the carrier device, and so on.

The optimal solution is to apply the bioactive agent in the absence of any containment or time release substance and from a layer which is predominantly or entirely made of bioactive agents. In this manner, after administration of the bioactive agent or agents, the medical device remains free of agent delivery substances (polymer layers, for example) and no unnecessary carrier substances are released into the patient's body. The problem, however, has existed with getting a bioactive agent to be held sufficiently well and reliably on the medical device.

The inventors have discovered that certain treatments of the medical device, and in particular the surface or surfaces of the device intended to be coated with one or more bioactive agents, can substantially increase the adhesion of the bioactive agent to the medical device before and during deployment of the device in the patient. Furthermore, the inventors have discovered that controlled formation of a pure, substantially contaminant free oxide layer on the surface can substantially increase the adhesive characteristics of the surface, to such an extent that it is not necessary to use other mechanisms to retain a bioactive agent on the device. The inventors have also found that the oxide layer may be tailored so as to bind to particular drugs especially well. For example, a more acidic polar oxide layer will bind well to a basic polar drug and vice versa.

As shown in FIGS. 6A and 6B a naturally formed oxide layer, that is at least partially formed by atmospheric contact, can result in the formation of an impure or non-uniform oxide, leading to non-uniform characteristics to the oxide and poor retention of bioactive material. This is typically resolved by using a containment layer or agent. It has not previously been considered that a uniform oxide layer could be formed on the structure of a medical device and in a manner that containment materials or layers could be avoided.

Where the base material is nitinol, the oxide layer formed using the method of the present invention will be predominantly titanium dioxide. When coated with PTX the oxide has a polar acidic nature, binding well to the polar basic PTX coatings. By forming a more pure titanium oxide layer, reducing the proportion of contaminant in the layer, the oxide layer is more polar acidic in nature and therefore binds better to polar basic coatings such as PTX.

The oxide layer may be modified further by addition of doping agents to be the conjugate of the polar characteristic of the bioactive material, or to be amphoteric. Thus, for a bioactive material which is a base (or predominantly a base) the oxide is formed to be more polar acidic. On the other hand, for a bioactive material which is acidic (or predominantly acidic) the oxide is formed to be more polar basic. The treatment provides a totality or preponderance of acid or base species of the at least one surface of the device intended to be coated or modified for other reasons. These form a characteristic to the device surface and provide a bonding site for the base or acid conjugate of the bioactive material. The acid or base species do not form a polymer matrix, for instance. Bonding of the bioactive agent is by means of covalent forces, in which the base/acid or acid/base combinations form a Lewis adduct. Bioactive material molecules which overlie those directly attached to their covalent species will bind to other bioactive material molecules by same species covalent bonds.

In practice, the treatment leads to an increase in the polar acid or polar base energy component of the surface or surfaces, which leads to a significant increase in the quality of adhesion of bioactive agent to the contact surface of the medical device also to a substantial improvement in uniformity of the contact surface(s) of the medical device.

A significant improvement in bioactive material retention is experienced by oxide layer modification alone. Better retention may be achieved in some cases by first cleaning the contact surface or surfaces of the medical device to remove impurities, generally acquired during and after the manufacturing process. This can substantially increase the amount of carbon functional groups on the contact surface(s) of the medical device, leading to an even more uniform coating of bioactive material across the contact surface of the medical device.

The specific embodiments described below are directed to a stent formed of nickel titanium alloy (for instance Nitinol) which is coated with paclitaxel, a preferred bioactive agent. The skilled person will appreciate that this is an example only and that the teachings herein are applicable to the other stent materials, including metals and metal alloys. The teachings herein are similarly not limited to stents only and can be applied to other medical devices of the types mentioned elsewhere in this specification.

Figure 3A:
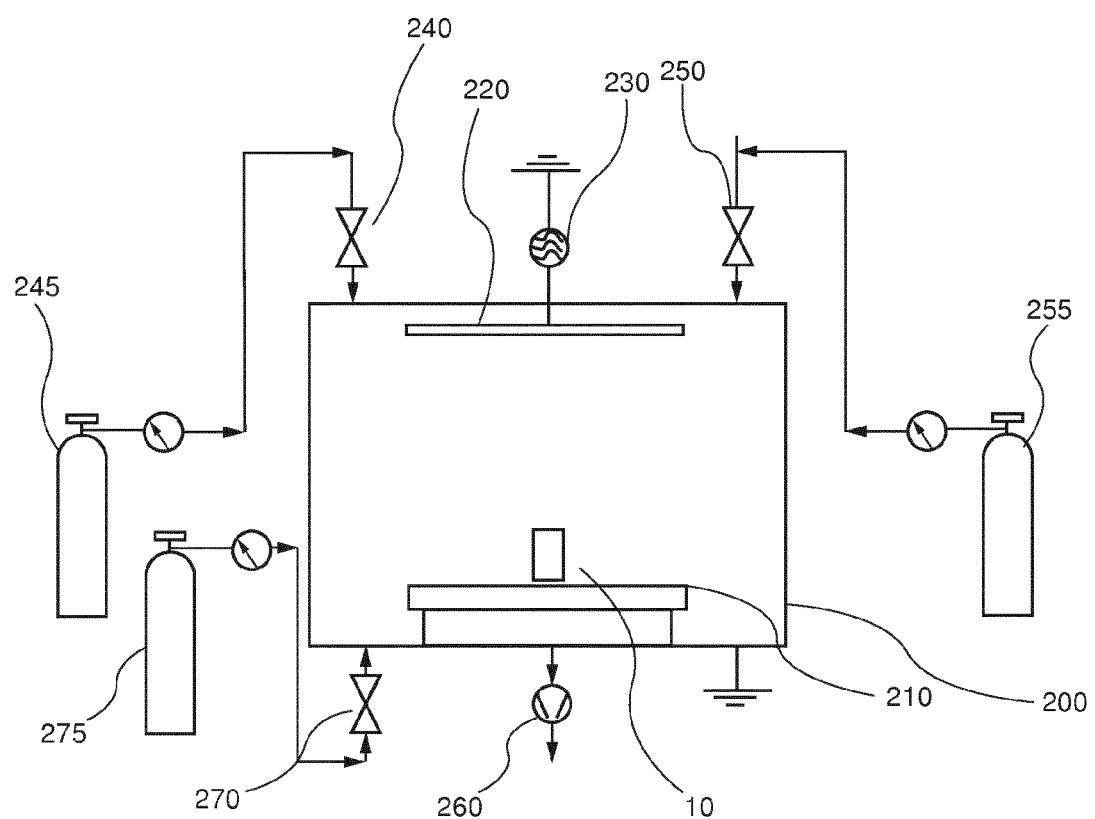
FIG. 3A is a schematic diagram of a plasma chamber apparatus used in the preferred method of forming a medical device according to the teachings herein.

Referring now to FIG. 3A, this shows a schematic diagram of a plasma chamber 200 apparatus for treating a stent 10 so as to grow in controlled manner the oxide on the stent surfaces in order to change the bonding characteristics of the surface. The treated oxide exhibits a very high percentage of titanium dioxide. The treatment suppresses the amount of nickel in the oxide layer, which the inventors have discovered adversely affects the retention of basic bioactive agents. In the inventors' experience nickel metal is basic while titanium oxide is acidic, as evidenced by the polar energy tests described below. Moreover, the treatment in the preferred embodiment eliminates contaminants such as carbon and/or calcium and other impurities in the oxide layer, resulting in a significantly more uniform oxide coating.

The new oxide layer is advantageously grown to be at least 3 nm thick. Where the oxide layer is substantially pure and uniform such a thickness may be sufficient to reduce the effect caused by variations in the underlying structure. The inventors have found that the preferred oxide layers produce a reliable performance which is practically unaffected by variations in the underlying structure. This is a significant benefit, both clinically and in meeting or exceeding regulatory specifications.

Any acidic species in the oxide layer increases the acidic polar component of the surface energy of the contact surface, providing good adhesion characteristics to the surface, for holding a bioactive agent (being the conjugate base) onto the contact surface. The same applies to the opposite arrangement of a polar basic oxide and the conjugate of a polar acidic bioactive material. The resulting structure is substantially better than what can be achieved with a non-modified contact surface of a medical device. Furthermore, this oxidation process increases the reliability of the overlying coat, in that a more consistent dosage of bioactive agent is applied on the contact surface during batch coating.

Even though it has been found that controlled formation of the oxide layer per se provides a notable increase in adhesion of a bioactive agent onto the medical device, cleansing of the contact surface or surfaces prior to oxidation can in some cases result in even better bioactive material retention on the medical device.

A preferred method described below in connection with FIGS. 3A, 3B and 4 treats a nickel titanium alloy stent. The alloy may be Nitinol, but in some embodiments the alloy is modified by the addition of one or more acidic or basic components.

Figure 3B:
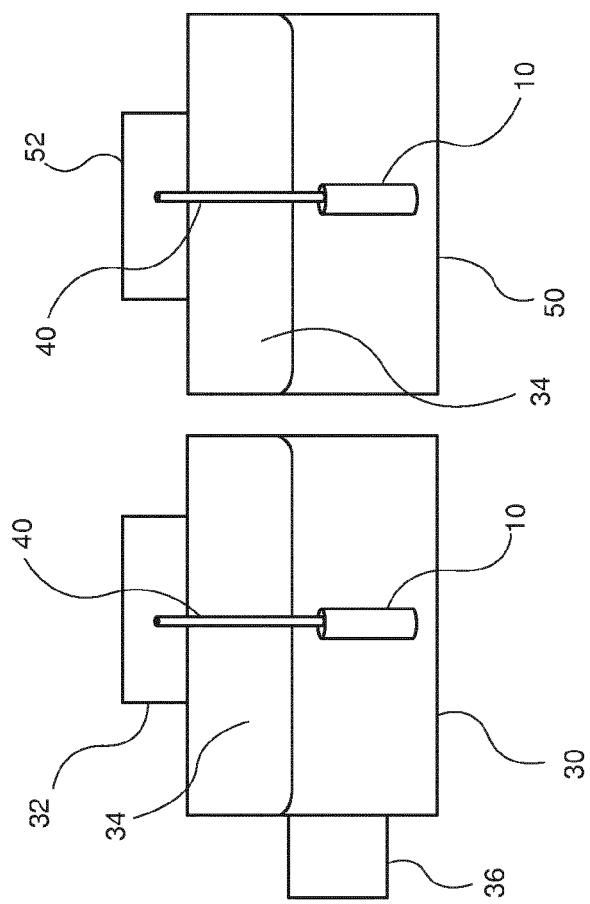
FIG. 3B is a schematic diagram of an electropolishing and neutralising apparatus used in a method of forming a medical device according to the teachings herein.
Figure 4:
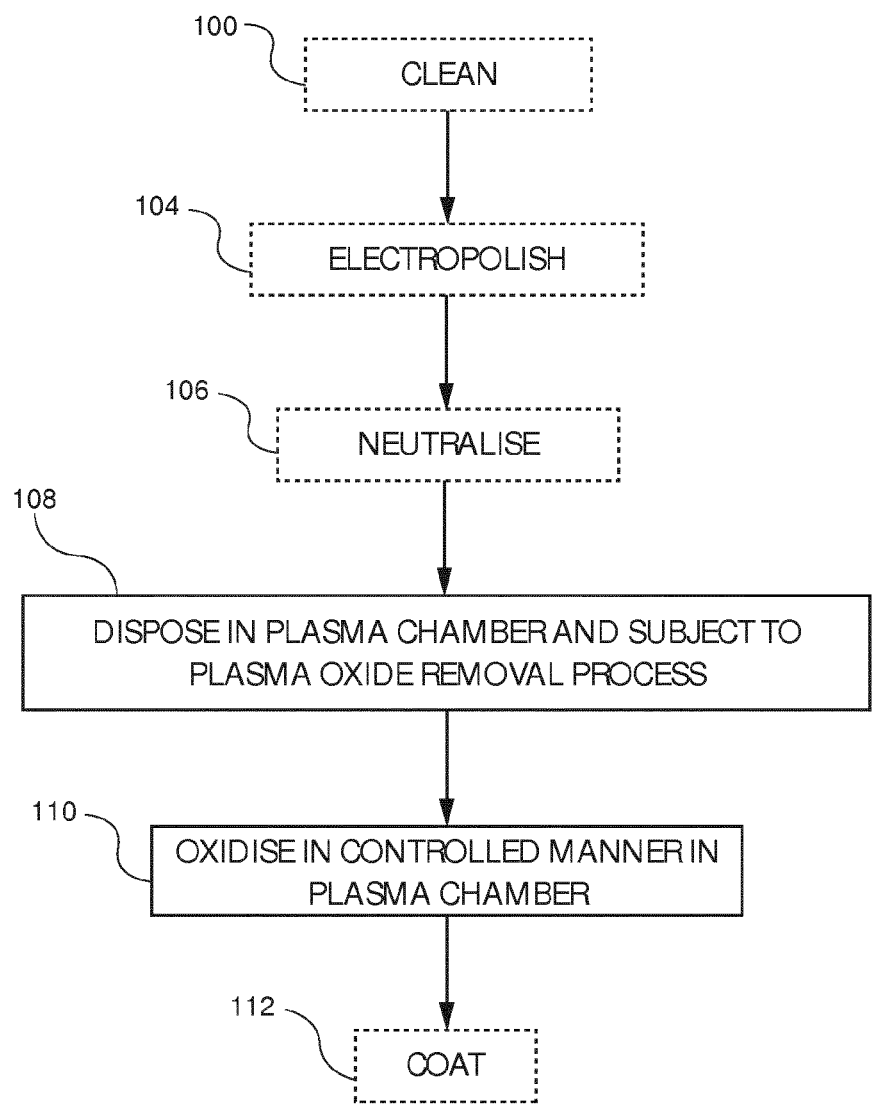
FIG. 4 is a flow chart of a preferred method.

FIGS. 3A, 3B and the accompanying description make reference to a stent 10. It is to be understood, though, that stents are often batch processed and that a plurality of stents will be treated simultaneously in each of the treatment stages. As batch processing of this nature is known, it is not described herein any further but it is to be understood that this is intended to form an integral part of this disclosure.

Prior to the treatment of the stent in the plasma chamber 200 apparatus shown in FIG. 3A, the stent may be cleaned in a one or multiple stage process, if it is found to be required. FIG. 3B is a schematic diagram of an electropolishing and neutralising apparatus which may be used prior to plasma removal of the oxide layer. A first cleaning stage (step 100 in FIG. 4) uses a variety of cleaning solutions, such as for example an alcohol solution including ethanol to remove larger and volatile impurities from the contact surface.

Second and third stages (steps 104 and 106 of FIG. 4) are electropolishing and neutralisation of the surface. The basic components of the apparatus and the method are shown in FIGS. 3A, 3B and 4. The skilled person will appreciate that the apparatus and method will include other components and steps standard in the art and which are not therefore described herein.

In the electropolishing stage 30 (and step 104 in FIG. 4) the stent 10, typically provided on a support such as a mandrel 40, is disposed into an etching solution, typically acidic, in the bath 30. This stage also includes the components 32 necessary for carrying out electropolishing and in this regard any suitable electropolishing device may be used, as is the case with the electropolishing fluid used in the bath 30. The electropolishing stage 30 (and step 104) is, preferably, operated to remove at least about 2%, at least about 10%, or at least about 20% up to at least about 30% by weight of the material of the stent 10, in order to etch away the exposed surfaces of the stent 10 to remove heat affected zones, in the course of which there are also removed surface containments and any natively formed oxide layer. The bulk material of the stent 10 is, in some embodiments, standard Nitinol.

In order to avoid further contamination of the stent 10, in particular at the end of the electropolishing process, above the electropolishing solution in the bath 30, that is in the top portion 34 of the chamber 30, there is preferably provided an inert gaseous blanket which does not contain oxygen or water. Suitable inert blankets could be argon or nitrogen gas or any other noble gas.

The stage 30 may be provided with a solution changing/cleansing unit 36 for cleaning/changing the electropolishing solution so that the stent can be exposed to clean solution. The unit 36 may include one or more sensors for sensing the state of the electropolishing solution.

The neutralisation stage 50 may have similar components to the electropolishing stage 30, and includes a solution of neutralisation fluid, typically a base compound, for washing and removing acidic components from the exposed surfaces of the stent. The neutralisation stage 50 will also typically include driving unit 52 of a type commonly known in the art. The stent 10 may be retained on the holder 40 during this process. The neutralisation bath 50 is also preferably provided with an isolation blanket 34 similar to that of the electropolishing stage 30 and this again may be of a noble gas such as argon, or nitrogen, for instance. The blanket 34 is preferably oxygen and water free.

As soon as the stent leaves the electropolishing acid bath a native oxide layer forms almost instantaneously on any exposed surfaces. Such an instantaneously produced oxide layer will typically have a thickness of around 3 nanometres. The composition of the native layer will be dependent upon a number of factors such as the nature of the bulk material, cleanliness of the electropolishing bath and of the stent itself going into the bath, purity of the gaseous blanket, how the stent is handled after electropolishing and the neutralising chemicals used, and the composition of the surrounding atmosphere at the time of oxidation. This may lead to an uneven oxide layer across the surfaces of the stent and can also result in the oxide layer having inconsistent characteristics such as by being contaminated with elements which will affect the performance of the oxide layer. For example, a native oxide is likely to contain significant quantities of carbon, and potentially calcium and silicon.

As described, following electropolishing the stent is oxidised naturally in the air. This is generally the state in which stents can be purchased from a manufacturer. The stent is then disposed in a plasma chamber 200, subjected to a plasma oxide-removal process (see step 108, FIG. 4) and then a new oxide layer is formed on the exposed surface (see step 110, FIG. 4).

The plasma chamber 200 includes a sample holder 210 for supporting a stent 10, an electrode 220 and high frequency generator 230 for stimulating matter to a plasma state. The apparatus includes a vacuum pump 260 for removing air from the chamber, so as to eliminate contaminants from the chamber and create a vacuum inside the chamber. The apparatus includes a hydrogen gas supply 245 and an argon gas supply 255, and valves 240 and 250 for controlling the flow of the gases into the plasma chamber 200. It will be appreciated that other gases may be used in their place, or in addition. In place of argon, for example, another noble gas may be used. The apparatus also includes an oxygen source 275 and an oxygen valve 270 for allowing a controlled flow of oxygen into the plasma chamber so as to form a new oxide on the stent surface. The plasma chamber 200 may be heated so as to control the rate of oxidation.

A variety of plasma cleaning systems may be used, for example a Diener Femto type B system, or a Diener Pico system having a 13.56 MHz generator and a quartz glass chamber. The electropolished stent is placed into the plasma chamber, and a vacuum is applied to the chamber to evacuate the system of contaminants and air. Hydrogen and/or argon gas is introduced into the plasma chamber 200 at flow rates of approximately 30 sccm and at an estimated pressure of 0.4 mbar. The high frequency generator is activated to stimulate the gases in the plasma chamber into a plasma state. The plasma chamber is set to 13.56 MHz & 100 Watts for 5 minutes. During this time the hydrogen and/or argon plasma removes the oxide layer and the argon plasma may even remove the nickel rich sublayer from the surface of the stent. The vacuum pump remains on throughout the oxide-removal process to remove matter from the plasma chamber. After the oxide layer has been removed the high energy source (plasma) is switched off and the gases are turned off by closing the valves. The chamber is evacuated using the vacuum pump.

Preferably, the hydrogen and argon gases are mixed together in a mixer valve before they enter the plasma chamber. This mixing results in a more uniform process.

The stent then remains in the plasma chamber, without exposing the stent to the atmosphere, and a new oxide layer is formed on the surface of the stent by introducing oxygen gas into the plasma chamber via the oxygen valve at a flow rate of approximately 30 sccm. During this step the plasma remains switched off. Preferably the oxygen is pure oxygen gas. The plasma chamber is preferably supplied with very small quantities of oxygen, into the chamber 200. This ensures controlled oxidation of the exposed surfaces of the bulk material of the stent 10. During formation of the new oxide layer the vacuum pump remains switched on so as to continue drawing matter from the chamber. The plasma source is switched off whilst the new oxide layer is formed. After formation of the new oxide layer the vacuum pump is switched off and the chamber is vented with oxygen gas before the stent can be removed for coating.

In some embodiments argon, or another noble gas, is also introduced into the plasma chamber at the same time as the oxygen gas. The noble gas is used to control the rate of oxidisation at the surface so as to ensure an even thickness oxide layer. Preferably, the oxygen and argon gases are mixed together in a mixer valve before they enter the plasma chamber. This mixing ensures production of a more uniform oxide layer.

Heat can be applied to the plasma chamber to optimise the oxide if required. Diffusion is temperature dependent. Titanium has to diffuse from the bulk metal and bond with oxygen. Nickel will also diffuse out from the bulk, but titanium will diffuse at a faster rate, covering over the nickel and resulting in titanium oxides at the surface. The predominantly titanium dioxide layer can have elemental nickel, and nickel oxide in it, but titanium dioxide should always dominate the outermost layer of the oxide. The higher the temperature the more diffusion occurs and the thicker the oxide will be.

A pure, substantially contaminant free and even thickness new oxide layer is formed on the surface of the stent. At this point the stents will have improved corrosion resistance due to the cleanliness of the oxide.

Following the formation of the oxide layer on the stent 10, the device may then be coated with a layer of bioactive material, for example paclitaxel or any of the other bioactive materials disclosed herein. This may be singularly or in combination with one or more other bioactive materials. The result is a significantly improved bioactive material coated medical device. If the stents are to be further coated it is preferred that they be transferred as fast as possible to the coating equipment, for example within one hour or at least in the same day, so as to avoid contamination of the new oxide layer. Parts may be stored in ultra-clean glass vials to prolong this period and avoid contamination.

The stent may be coated (step 112 in FIG. 4) by any of a variety of systems including, for example, dipping, spraying and rolling. The bioactive material may be provided in pure form but more typically in solution or suspension in a volatile solvent such as ethanol or the like. The bioactive material may be coated onto the exposed surfaces of the stent 10 in one or more passes, in dependence upon the amount of bioactive material to be applied to the stent 10. Dipping will be typically be a single pass, although it is not excluded that the stent may be dipped in a multiple of times. Spraying and rolling may more commonly involve multiple passes.

The bioactive material coating is dried at the end of the coating stage and may also be dried between passes in a multiple-pass coating process. Drying may be by natural drying or forced drying.

The oxidised stent may optionally be cleaned prior to coating (step 112 in FIG. 4), although this will be dependent upon the nature of the handling of the stent 10 following its oxidation. For example, if the stent has been stored for some time after formation of the new oxide layer, it may be preferable to clean it before use. Such cleaning may be with an alcohol such as ethanol or with a weak plasma to remove any carbon deposits or other non-volatile deposits without removing any of the oxide layer.

Instead of, or in addition to, doping the oxide, it is contemplated that polar acidic or polar basic components could be added to the bulk material of the stent, in this example to the nickel titanium alloy of the stent. In accordance with the example given above, this may be by the addition of magnesium, aluminium, cerium, zinc, molybdenum, tungsten, niobium, tantalum, vanadium, zirconium, in concentrations typically less than 1000 parts per million as a dopant or in greater concentrations as an alloying element into the bulk material. These components are not designed to effect the structural characteristics of the bulk material, in this case to act as a shape memory alloy, but to effect the characteristics of the subsequently formed oxide layer, by the drawing out of these components from the bulk material to the surface and then into the oxide layer in order at stage 60, in order to provide the oxide layer with a polar acidic or polar base characteristic.

Figure 5:
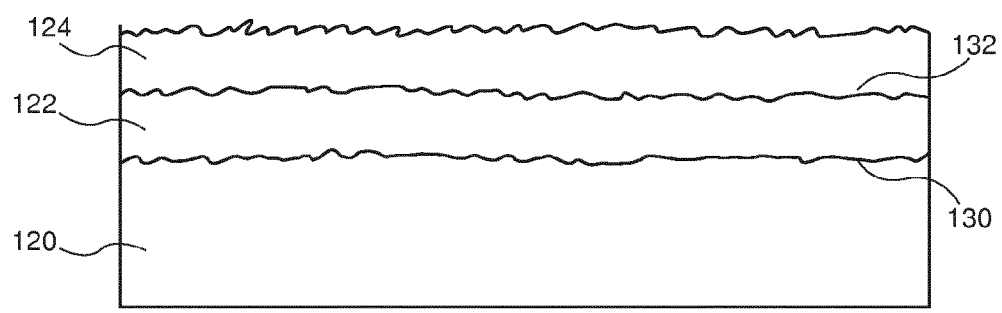
FIG. 5 is a schematic diagram of a transverse cross-sectional view of a stent strut of the stent of FIGS. 1 and 2 to show the oxidised contact surface and bioactive material coating.

Referring briefly to FIG. 5, this shows a transverse cross-sectional view of a stent, such as the stent 10 shown in FIGS. 1, 2 and 3A and 3B. The tubular structure 12 of the stent, in particular strut 120, thereof has had its oxide layer 122 formed in the manner taught herein, so as to be amphoteric or to be polar acidic or polar basic. Bioactive agent 124 is deposited onto the oxide layer 122 (for example by spraying, rolling or dipping). It is not necessary to embed the bioactive agent in any containment matrix or layer, as is done in the prior art. It is preferred that the bioactive agent layer 124 is distinct from the base support (formed of the structure 120 and oxide 122). Thus, the exposed surface of the bioactive material layer 124 is solely the bioactive material (and possibly any functional groups included with it, such as excipients and so on).

At the interstice 130 between the bulk material 110 of the structure of stent 10 and the formed oxide layer 122 there may be remnants of contaminant materials, for example silicon. However, the electropolishing process will remove the majority of any such contaminants, including silicon, and at worst there may be some slight residue with crevasses on the surface of the bulk material. However, these will be minor and not affect the functional characteristics of the bulk material or of the subsequently formed oxide layer. Similarly, at the interstice 132 between the oxide layer 122 and the layer of bioactive material 124 there may be some minor residue of contaminants. Again, by controlled handling this can be minimised.

The oxide layer 122 of the stent 10, having a high polar acid or polar base characteristic, readily attracts its conjugate bioactive agent. This provides a uniform and consistent coating of bioactive agent across the contact surface or surfaces of the stent and therefore a consistent dosage of bioactive agent. Furthermore, it is possible in some cases to load a greater amount of bioactive agent to the contact surface of the stent.

The higher surface energy of the stent permits a greater variety of coating methods, given the greater adhesive characteristics of the oxide surface(s).

Although the method and system described above and in conjunction with treatment of a stent, the same method and system can be used to treat other medical devices.

In some cases it may be preferred that the bioactive agent is released quickly into the patient's tissues and for this purpose an excipient, such as urea and/or urea derivatives, gallates and gallate derivatives (such as epi gallo catechin gallate), saccharides and/or saccharide derivatives, chitin and/or chitin derivatives, ascorbic acid, citric acid, sterates and/or sterate derivatives, polyvinyl pyrolidone, dicalcium phosphate dihydrate, eudragit polymers and/or eudragit polymers derivatives, cellulose and/or cellulose derivatives, PEG, poylsorbate 80, sodium lauryl sulphate, chitosan, magnesium dioxide, silicon dioxide, carbonate derivatives, plasdone, butylated hydroxyanisole, succinic acid, sodium dioctyl sulfosuccinate, precirol ATO 5, may be added to the bioactive agent. The excipient will speed up the release of the bioactive agent once the medical device is deployed within the patient, for instance by the excipient dissolving within the patient's blood plasma and providing for quick release of the bioactive agent. When an excipient is used, this may be as a sublayer between the layer of bioactive material and the medical device or as a layer above the layer of bioactive material. The excipient acts to speed the release of the bioactive agent (drug for example), compared to a drug per se or a drug held in a containment or time release layer. In the case of a sublayer of excipient, the functionalisation of the surface to be coated will be matched to the nature of the excipient and the excipient matched to the bioactive agent or agents.

The bioactive material can be any of a large variety and many bioactive materials for coating medical devices are known in the art. The layer of bioactive material applied to the functionalised surfaces of the device may be of a single bioactive material or a combination of different bioactive agents, in dependence upon the desired treatment. There may also be provided other active agents in the bioactive material layer, such as excipients or other release facilitators.

The bioactive material of the coating may include at least one of: paclitaxel and/or paclitaxel derivatives, rapamycin and/or rapamycin derivatives, docetaxel and/or docetaxel derivatives, cabazitaxel and/or cabazitaxel derivatives, taxane and/or taxane derivatives, estrogen or estrogen derivatives; heparin or another thrombin inhibitor, hirudin, hirulog, argatroban, D-phenylalanyl-L-poly-L-arginyl chloromethyl ketone or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; an antimicrobial agent or antibiotic; aspirin, ticlopdine or another antiplatelet agent; colchicine or another antimitotic, or another microtubule inhibitor; cytochalasin or another actin inhibitor; a remodelling inhibitor; deoxyribonucleic acid, an antisense nucleotide or another agent for molecular genetic intervention; GP IIb/IIIa, GP Ib-IX or another inhibitor or surface glycoprotein receptor; methotrexate or another antimetabolite or antiproliferative agent; an anti-cancer chemotherapeutic agent; dexamethasone, dexamethasone sodium phosphate, dexamethasone acetate or another dexamethasone derivative, or another anti-inflammatory steroid; dopamine, bromocriptine mesylate, pergolide mesylate or another dopamine agonist; 60Co (having a half life of 5.3 years), 192Ir (73.8 days), 32P (14.3 days), 111In (68 hours), 10 90Y (64 hours), 99 mTc (6 hours) or another radio therapeutic agent; iodine containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting 15 enzyme (ACE) inhibitor; ascorbic acid, alphatocopherol, superoxide dismutase, deferoxyamine, a 21-aminosteroid (lasaroid) or another free radical scavenger, iron chelator or antioxidant; angiopeptin; a 14C-, 3H-, 131I1-, 32P- or 36S-radiolabelled form or other radio labelled form of any of the foregoing; or a mixture of any of these.

The preferred embodiments described above relate to a nickel titanium alloy stent. Other examples are stainless steel, cobalt chromium and cobalt platinum stents. In these cases, the oxide is preferably formed primarily of $Cr_2O_3$. These examples of stent may also be subjected to doping of the oxide and/or of the bulk material in the manner described above.

The teachings herein provide a medical device which is more resistant to corrosion.

The teachings herein also make it possible to attach bioactive agents to the surfaces of medical devices without having to rely on binding agents or polymer of other matrix materials as in the prior art. Binding agents are considered to be substances which enhance the adhesion of a bioactive material layer at the support surface and generally act to retard the release of the bioactive agent or agents. A polymer or other matrix performs a similar role. Binding agents and matrices act as containment mechanisms.

It may be desirable to form hydroxyl groups at the surface of an implantable device to improve bonding with a bioactive material coating. Many implantable alloys (SS304, SS316, CoCr, Nobel metal alloys, NiTi and other titanium based alloys) can be hydroxylated, as can many implantable polymers. The hydroxides of the transition metals and post-transition metals usually have the metal in the +2 (M=Mn, Fe, Co, Ni, Cu, Zn) or +3 (M=Fe, Ru, Rh, Ir) oxidation state. None are soluble in water, and many are poorly defined. One complicating feature of the hydroxides is their tendency to undergo further condensation to the oxides, a process called olation. Hydroxides of metals in the +1 oxidation state are also poorly defined or unstable. For example, silver hydroxide Ag(OH) decomposes spontaneously to the oxide ($Ag_2O$). Copper(I) and gold(I) hydroxides are also unstable, although stable adducts of CuOH and AuOH are known. The polymeric compounds $M(OH)2$ and $M(OH)3$ are in general prepared by increasing the pH of an aqueous solutions of the corresponding metal cations until the hydroxide precipitates out of solution. On the converse, the hydroxides dissolve in acidic solution. Zinc hydroxide $Zn(OH)2$ is amphoteric, forming the zincate ion $Zn(OH)42-$ in strongly alkaline solution.

Some metals, e.g. V, Cr, Nb, Ta, Mo, W, tend to exist in high oxidation states.

Rather than forming hydroxides in aqueous solution, they convert to oxo clusters by the process of olation, forming polyoxometalates.

Acid-base properties are of considerable importance in the interaction between polar organic molecules and oxide surfaces and play an important role in phenomena such as corrosion inhibition and the adhesive behaviour. The presence of a hydroxylated surface also plays a significant role in the interaction of oxide surfaces with ambient water vapor. Water vapor adsorbs onto the outermost hydroxylated layer by forming a hydrogen bonded network on the hydroxylated surface. Thus, the nature of surface hydroxyls on metal oxide films is important in a number of surface phenomena involving metals. Not only are the acid-base properties of an oxide film of great interest, but so too is the surface concentration of the hydroxyl groups. There have been numerous studies on determination of the concentration of surface hydroxyls. However there have been few studies on the quantitative determination of the concentration of surface hydroxyl groups on low-area oxide covered metals, i.e. sheets or foils.

Figure 8:
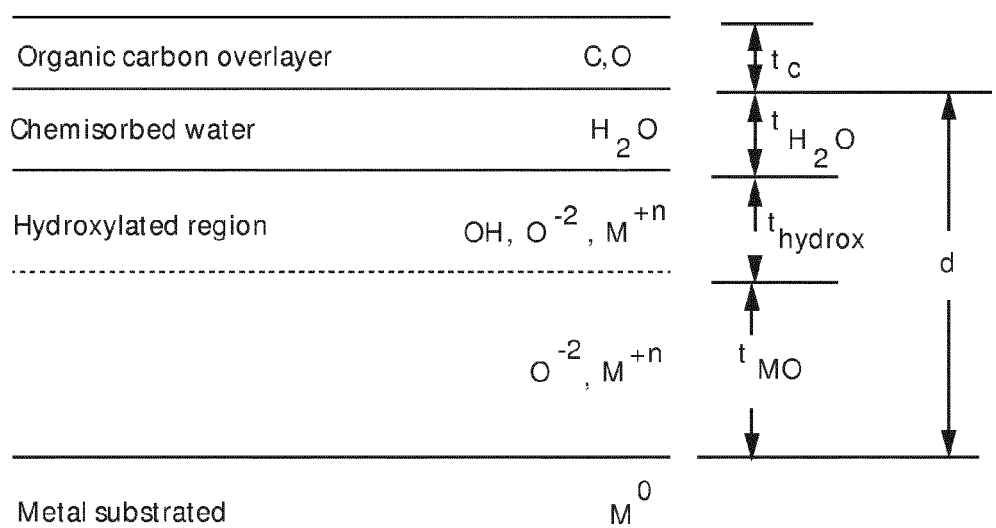
FIG. 8 is a schematic diagram for the model of an oxide-covered metal showing the various layers and their composition.

The surface oxide film on any given metal can be represented by the system shown in FIG. 8. The oxide film of thickness d consists of an outermost layer of chemisorbed water, a hydroxylated region of depth $t_{hydrox}$ and the innermost portion of the oxide film of depth $t_{MO}$. The entire oxide film is covered by an overlayer of adsorbed organic contamination of thickness $t_c$. This layer is referred to as carbon contamination. It has been assumed that the thickness of the hydroxylated region is due to a single layer of OH groups, i.e. up to 2.7 Å in thickness. This assumption does not hold for all metals. With aluminum for example, exposure to humid air produces a thickened hydroxide layer.

It is important to note that the outermost layer of organic carbon contamination includes oxygen-containing functional groups, i.e. C—O and O—C=O species which can complicate XPS analysis of the thickness of the OH and water layers. McCafferty and Wightman report the following corrected or compensated values for titanium in table 1 clearly identifying that the hydroxyl region was consistently 9.5 Å in thickness no matter the pre-treatment. Corrections required can be appreciable if the level of surface contamination is high. The correction decreases with a reduction in carbon contamination after either argon plasma treatment or sputtering of the carbon overlayer.

TABLE 1

The XPS binding energies for titanium metal/metal oxide systems with thickness calculations for the oxide and hydroxyl region.

| Surface treatment | Thickness of oxide film (Å) | Depth of hydroxyl region $t_{hydrox}$ (Å) | $I_{OH}/I_O$ |
|---|---|---|---|
| As received | 48 | 9.5 | 0.562 |
|  | 42 | 9.5 | 0.528 |
| Ultrasonic cleaned | 40 | 9.5 | 0.367 |

TABLE 1-continued

The XPS binding energies for titanium metal/metal oxide systems with thickness calculations for the oxide and hydroxyl region.

| Surface treatment | Thickness of oxide film (Å) | Depth of hydroxyl region $t_{hydrox}$ (Å) | $I_{OH}/I_O$ |
|---|---|---|---|
| Argon plasma | 32 | 9.5 | 0.559 |

Figure 9:
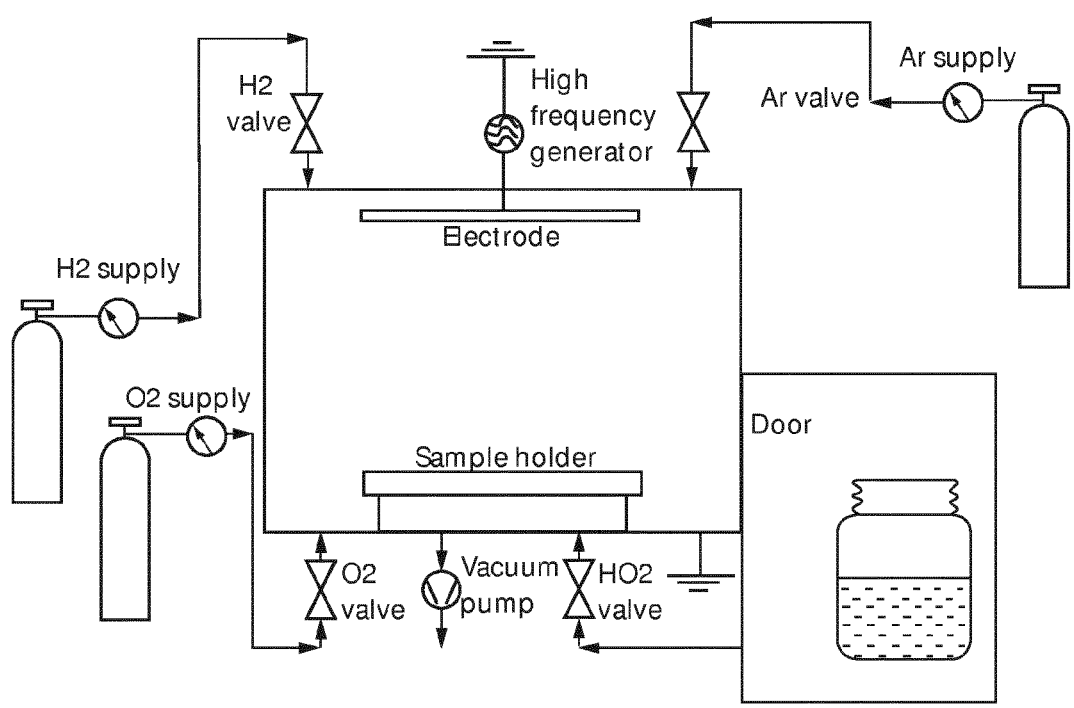
FIG. 9 is a schematic diagram of an apparatus including a water bath for dunking the stents into liquid water after the plasma process.
Figure 10:
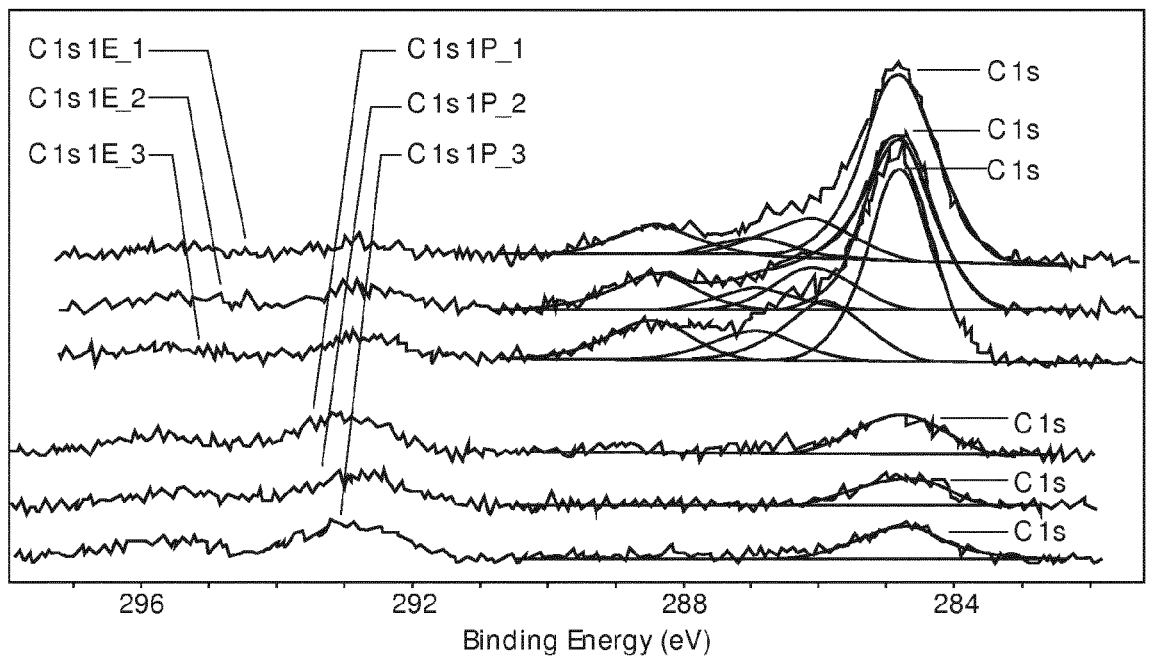
FIGS. 10 to 15 show XPS quantification of OH and water on NiTi oxide surface.
Figure 11:
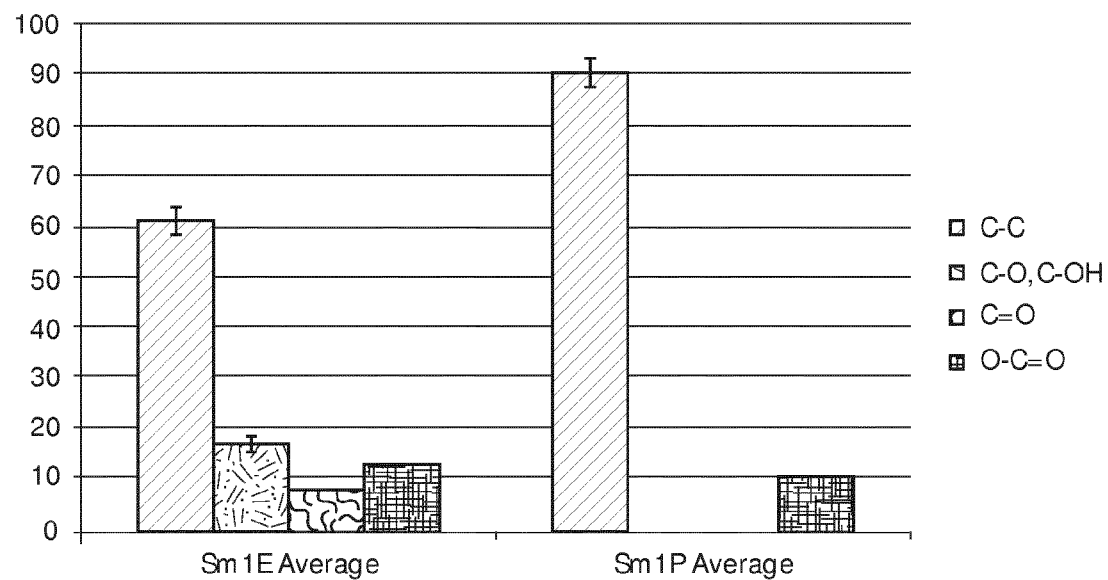
Figure 12:
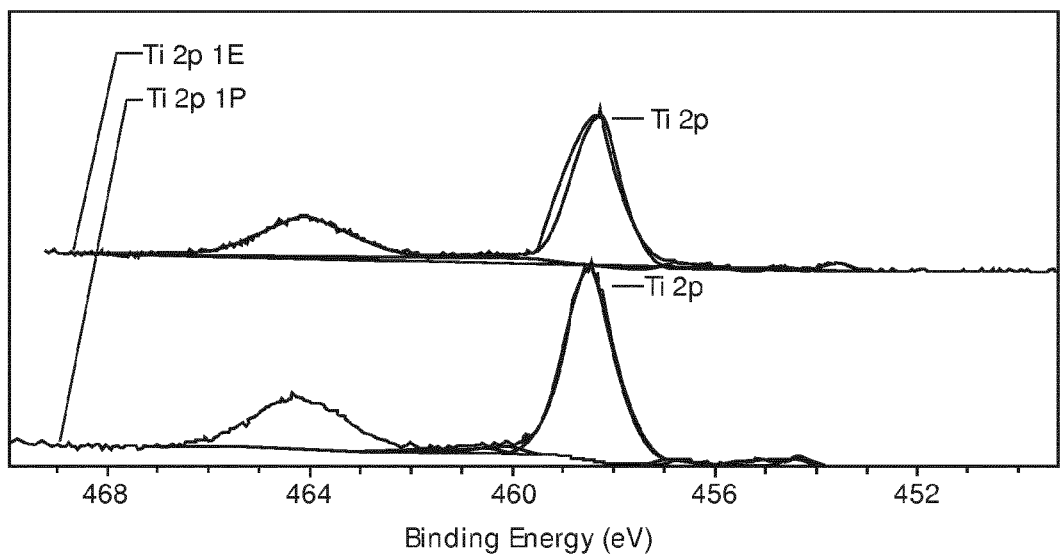
Figure 13:
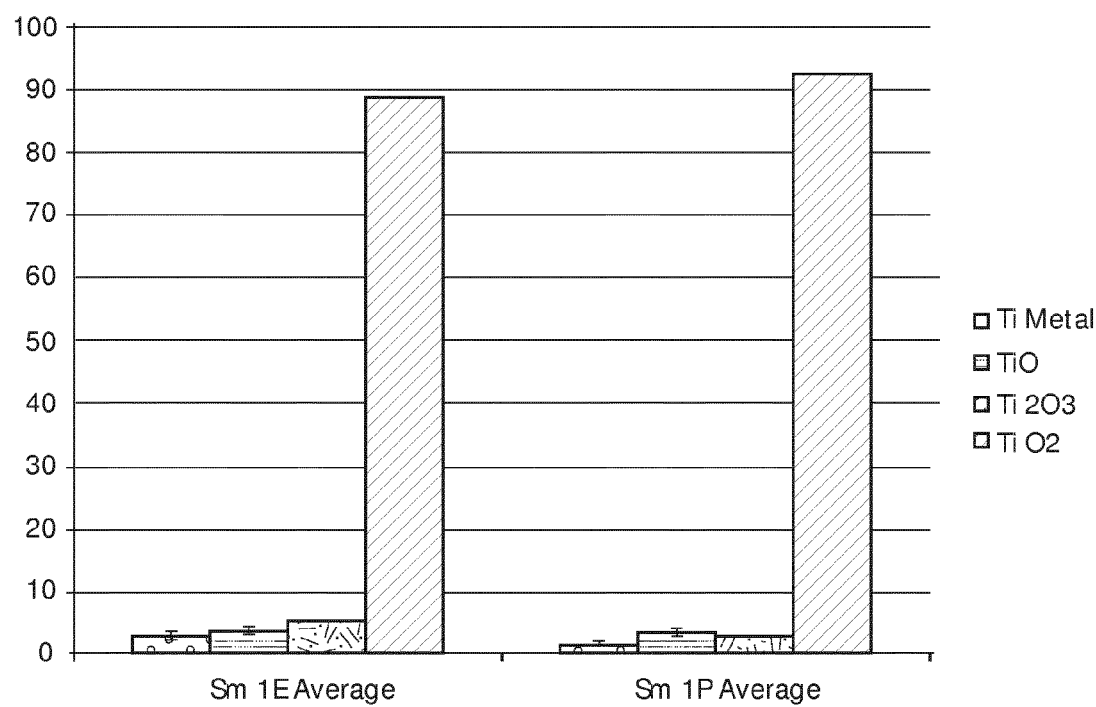
Figure 14:
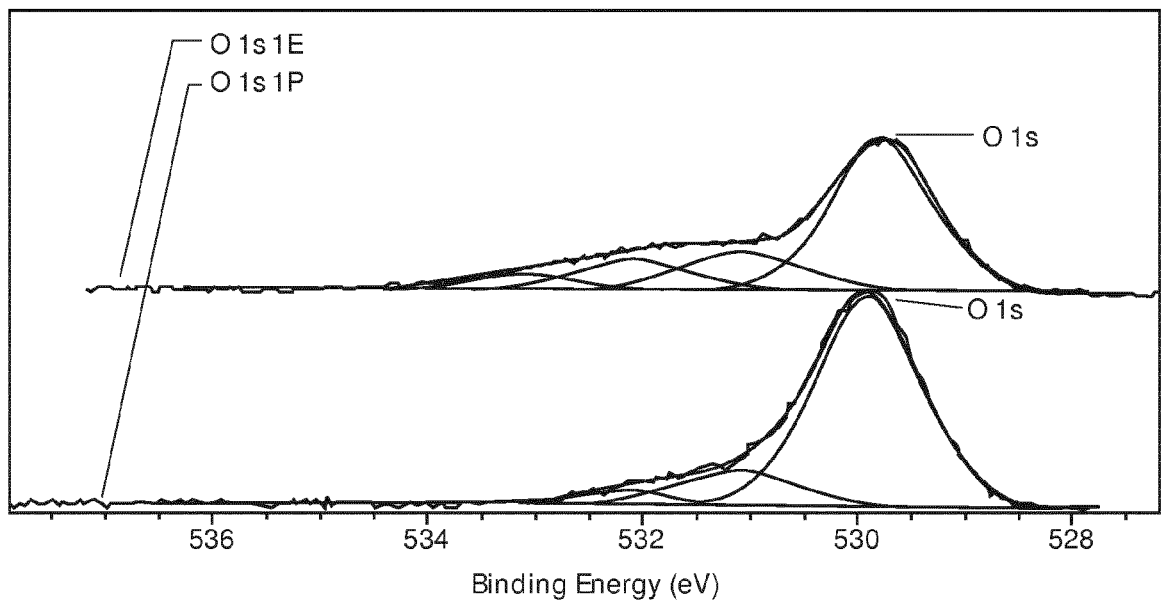
Figure 15:
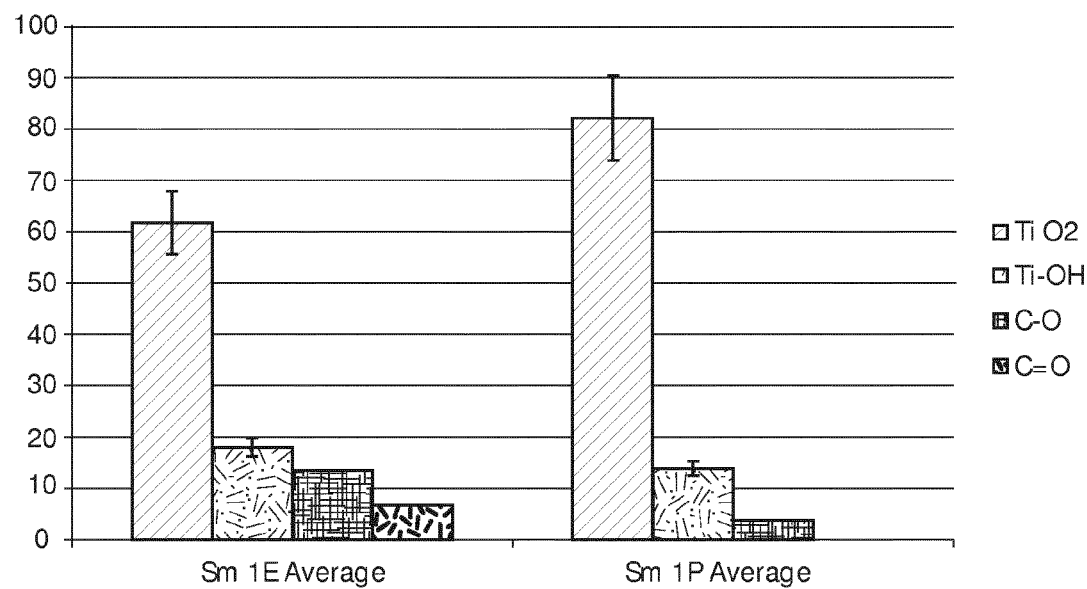

Hydroxyl (OH) groups may be formed at the surface of a metal oxide by the following process:
1. Plasma cleaning with H₂O vapour is designed to remove volatile and non-volatile contamination on the surface of stents including carbon
2. Stable OH formation occurs on stent surfaces in the plasma processes in the following possible ways:
   a. Directly after the plasma is turned off as H₂O is still being supplied into the chamber and the surface will have enough energy and dangling bonds to dissociate the water molecule creating OH
   b. In a similar manner to 'a' but the 0 and H molecules may be present in the plasma chamber left over from the plasma process
   c. By dunking the stents into liquid water after the plasma process without exposing them to atmosphere beforehand
   d. After the cleaned parts have been removed from the plasma chamber into the atmosphere assuming a non H and O gas is used during the plasma treatment and subsequent venting of the chamber FIG. 9 shows a plasma chamber setup including a water bath in which stents can be 'dunked' into water post plasma cleaning or oxide removal without exposing them to the atmosphere beforehand. Water can be supplied via the H₂O valve. Water vapour will be created when the water vapour valve opens and the pressures begin to equalise to the main chambers pressure (0.4 mbar) and 100 sccm flow rate. The pressures will never actually equalise, due to the constant vacuum being applied to the main chamber and H₂O valve restriction between the main chamber and the side chamber. In effect the vacuum created in the main chamber will constantly draw water vapour from the side chamber. The water vapour is used as the plasma gas during plasma cleaning.

When the vacuum is turned off in the main chamber, the H₂O valve can now be used to equalise the pressures. After which point the door between the chambers can be opened and the stents dunked into the bottle with water inside. The stents can be stored in this bottle until the next process keeping them free of contamination. Hydroxyl groups (OH groups) will form on the stents following these hydrolysis equations of titanium in an aqueous solution:

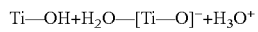

Ti—OH+H₂O—[Ti—O]⁻+H₃O⁺

Ti—OH+H₂O⁻[Ti—OH₂]+OH⁻

FIGS. 10 to 15 show XPS quantification of OH and water on NiTi oxide surface after the surface has been washed with ethanol, and after it has been plasma cleaned. In the figures E=ethanol wash and P=plasma. The results obtained highlight the efficiency of plasma in removing or reducing carbon contamination depending on its state. They show that the oxide remains relatively unaffected and that Ti-OH is formed after plasma treatment without the carbon contamination over layer.

Figures 16, 17:
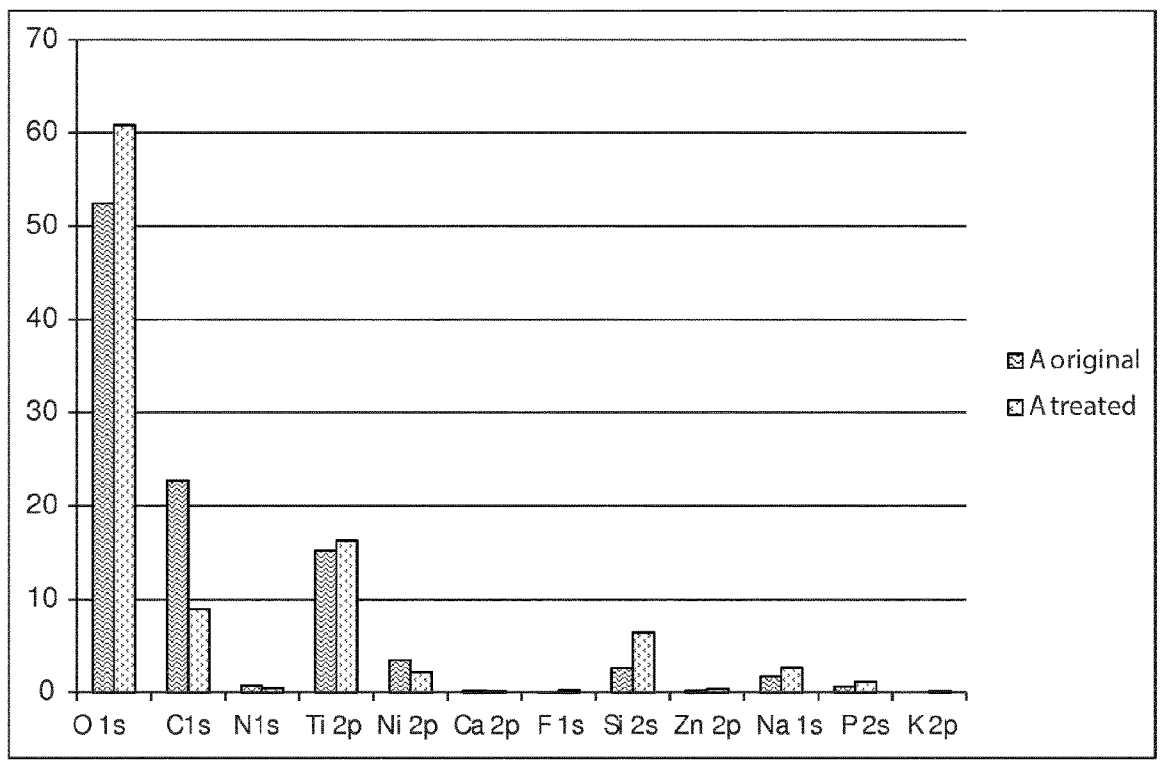
Figure 18:
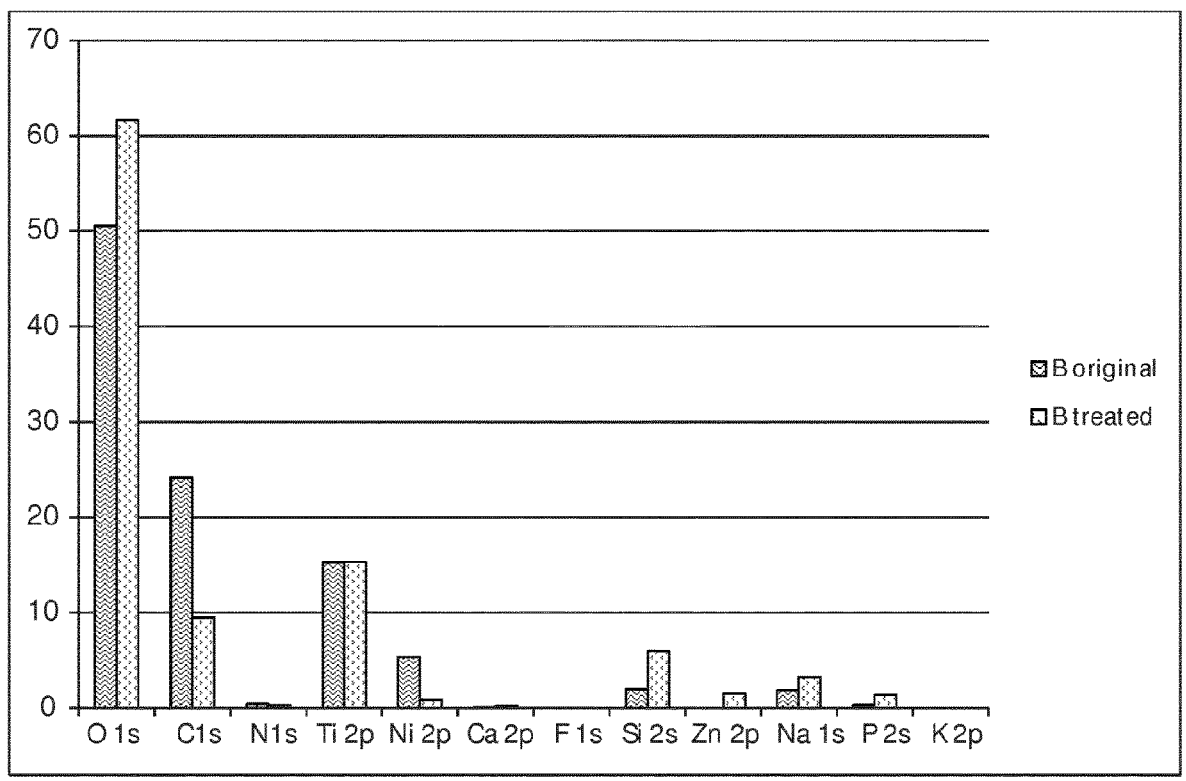
Figure 19:
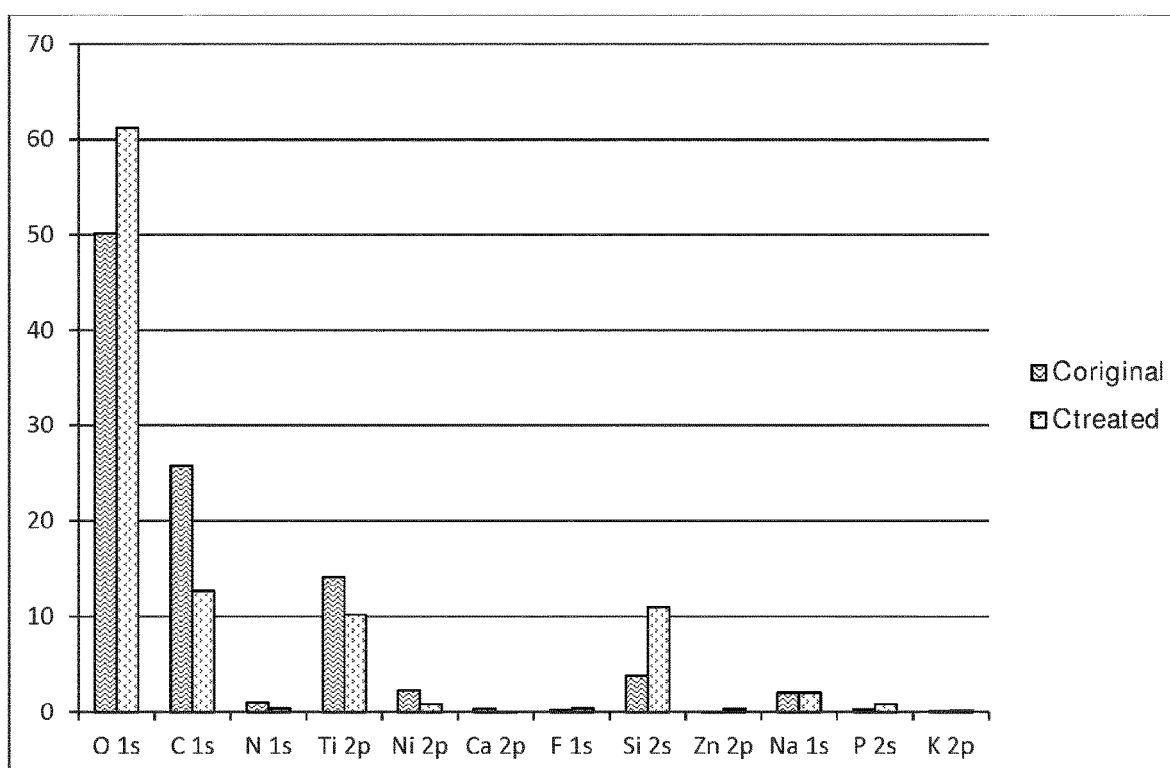
Figure 20:
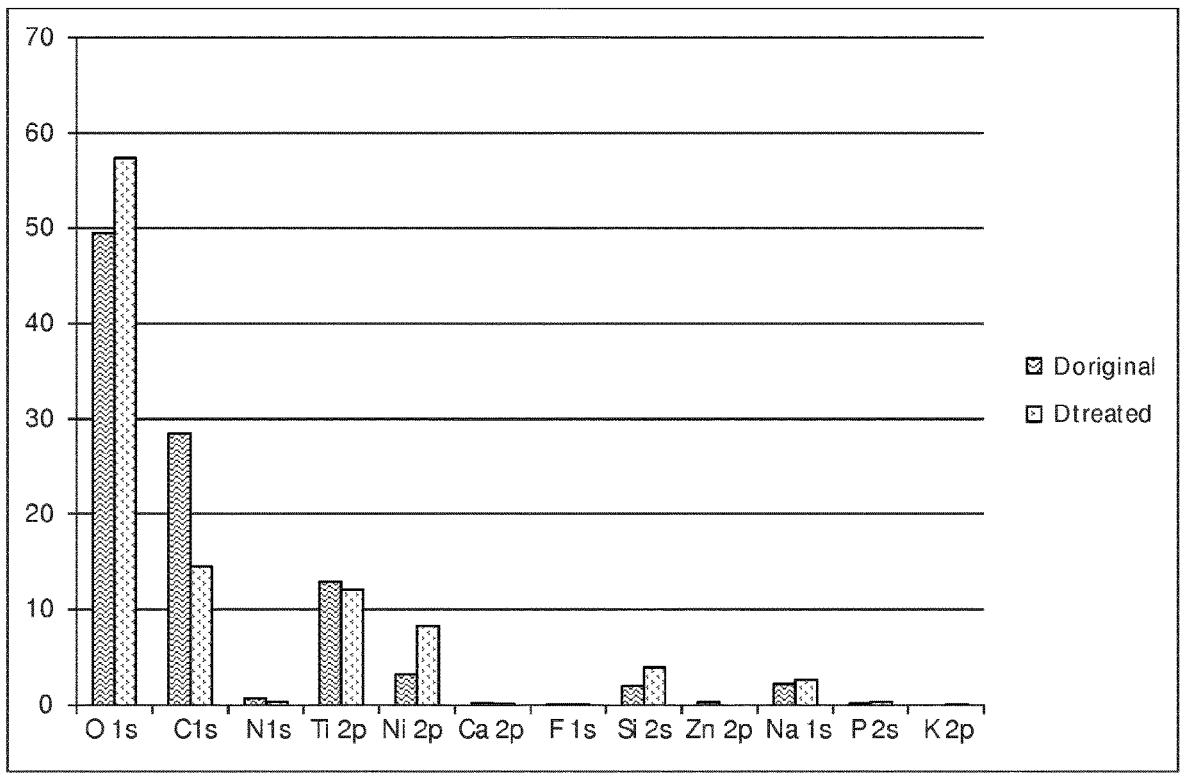

FIG. 16 is a table showing treatment conditions for four stents, A, B, C and D in a plasma chamber whilst removing the oxide layer from the surface of the stents and regrowing a new oxide layer at that surface. The machine used was the Diener Pico machine. This has a 13.56 MHz generator and a quartz glass chamber. The Pico system is a low-pressure system which has been found to be particularly useful for treating the intricate surface of a stent. As the plasma is in effect floating all around the stent, it can easily reach all surfaces of the stent to remove the oxide layer from the surface.

The inventors found that in a single batch of stents received from one manufacturer, the chemical composition of the surfaces of the individual stents within the batch could vary hugely. In particular the nickel content of the surface of the stent varied a lot. Due to the differences between the surfaces of the stents each stent was cut in half, one half was treated, and the other half left untreated. In this way the true result of the oxide removal and regrowth process on a given surface can be seen. FIGS. 17-20 show XPS data for the surfaces of stents A, B, C and D. The two columns in each graph compare the surface of one half of the stent as received (original), with the surface of the other half of the stent once treated in the plasma chamber under the conditions shown in the table of FIG. 16.

The XPS data shows that the original oxide layer has been removed from the stent and a new purer oxide layer has been grown on the surface. For a nitinol stent the surface is usually thought to be TiO₂, but it is not as simple as that. NiO₂ is also present and as the oxide layer thickens it can trap other contaminants in the oxide layer, such as elemental nickel, calcium, and other contaminants. As seen in the XPS data, there is less nickel present at the surface on the stent after the stent has been treated. This means that the contaminated oxide layer must have been removed, and replaced with a new purer oxide layer of TiO₂. In addition to the decrease in nickel, the inventors have also observed a greater decrease in carbon contamination than was achieved simply by plasma cleaning alone. The surfaces treated according to the invention show the lowest amount of carbon at the surface that they have seen to date. This supports the idea that the original contaminated oxide layer has been removed and replaced with a new purer oxide layer.

Figure 21:
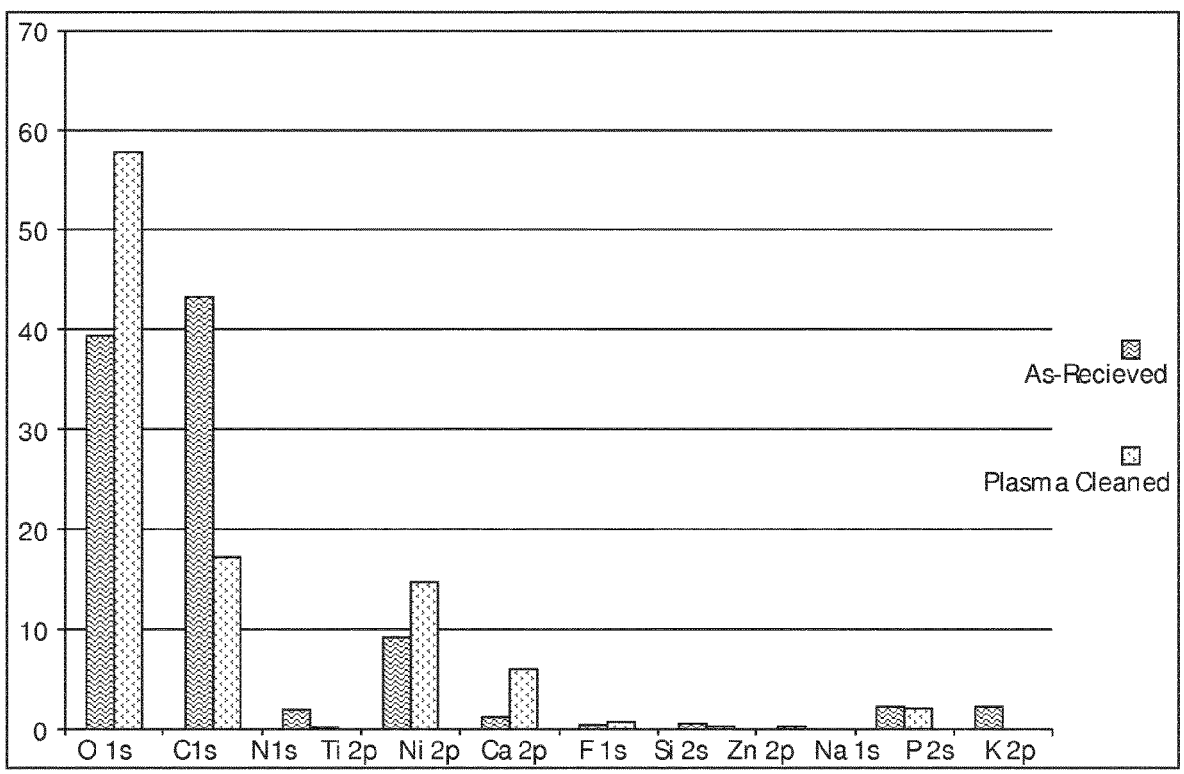
FIG. 21 shows comparable XPS data for a plasma cleaned surface.

FIG. 21 shows XPS data for plasma cleaned stent surface, compared with the surface of the same stent as received (original). When the inventors simply plasma cleaned a surface, without regrowing a new oxide layer at the surface (as shown in FIGS. 10-15), they observed a smaller decrease in carbon contamination at the surface, and an increase in nickel and titanium at the surface of the stent in the XPS data. It is thought that this is because the metal underneath the oxide is exposed during cleaning.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosure in the abstract accompanying this application is incorporated herein by reference.

The invention claimed is:

1. An endoluminally deployable implantable medical device having a structure for endoluminal implantation or disposition inside a vessel of a patient, the structure including:
   a bulk material; and an oxide layer disposed over at least one surface of the medical device;

wherein the oxide layer is substantially pure and free from contaminants;

wherein the oxide layer is carbon/calcium free; and a coating including a therapeutic substance applied directly on the oxide layer.

2. The medical device according to claim 1, wherein the oxide layer is between about 3 and 18 nm in thickness.

3. The medical device according to claim 1, wherein the bulk material is a nickel titanium alloy.

4. The medical device according to claim 1 wherein the medical device is or includes a stent.

5. The medical device according to claim 4, wherein the therapeutic substance is an anti-proliferative substance.

6. The medical device according to claim 5, wherein the anti-proliferative substance is paclitaxel.

7. The medical device according to claim 1, wherein the therapeutic substance is an anti-proliferative substance.

8. A vascular stent, comprising:

a metal alloy stent structure, the stent structure having at least one surface provided by the metal alloy; and an oxide layer at the at least one surface of the metal alloy stent structure, the oxide layer free from organic carbon contamination including C—O and O—C=O groups and free from Si contamination in the form of silicon oil; and a coating including a therapeutic substance applied directly on the oxide layer.

9. The vascular stent according to claim 8, wherein the oxide layer has no level of carbon or calcium detectable by X-ray photoelectron spectroscopy.

10. The vascular stent according to claim 9, wherein the oxide layer has a thickness between about 2 nm and 50 nm.

11. The vascular stent according to claim 10, wherein the thickness is between 3 and 18 nm.

12. The vascular stent of claim 10, wherein the oxide layer is passivated.

13. The vascular stent of claim 8, wherein the metal alloy stent structure is a nitinol stent structure, and wherein the oxide layer has an acidic polar surface energy of at least about 3.7 Dynes/cm and no measurable basic polar energy.

14. The vascular stent of claim 8, wherein the metal alloy stent structure is a nitinol stent structure, and the nitinol stent structure is free of a nickel rich sublayer under the oxide layer.

15. The vascular stent of claim 8, wherein the therapeutic substance is an anti-proliferative substance.

16. The vascular stent of claim 15, wherein the anti-proliferative substance is paclitaxel.

17. The vascular stent of claim 15, wherein the coating is constituted predominantly of the therapeutic substance.

18. The vascular stent of claim 15, wherein the coating consists of the therapeutic substance.

19. The vascular stent of claim 15, wherein the coating is free of time control release agents.

* * * * *